US009200080B2

(12) United States Patent
Saragovi et al.

(10) Patent No.: US 9,200,080 B2
(45) Date of Patent: Dec. 1, 2015

(54) AGONISTIC ANTIBODIES TO TRKC RECEPTORS AND USES THEREOF

(76) Inventors: Horacio Uri Saragovi, Montreal (CA); Véronique Guillemard, Bourail (FR); Neil Cashman, Vancouver (CA)

(*) Notice: Subject to any disclaimer, the term of this patent is extended or adjusted under 35 U.S.C. 154(b) by 0 days.

(21) Appl. No.: 13/820,715

(22) PCT Filed: Nov. 30, 2010

(86) PCT No.: PCT/CA2010/001906
§ 371 (c)(1),
(2), (4) Date: Sep. 19, 2013

(87) PCT Pub. No.: WO2012/027821
PCT Pub. Date: Mar. 8, 2012

(65) Prior Publication Data
US 2014/0004119 A1    Jan. 2, 2014

Related U.S. Application Data

(60) Provisional application No. 61/379,780, filed on Sep. 3, 2010.

(51) Int. Cl.
*A61K 39/395* (2006.01)
*C07K 16/28* (2006.01)
*C07K 16/40* (2006.01)
*G01N 33/566* (2006.01)
*A61K 45/06* (2006.01)

(52) U.S. Cl.
CPC ............. *C07K 16/40* (2013.01); *A61K 39/3955* (2013.01); *A61K 45/06* (2013.01); *C07K 16/2863* (2013.01); *G01N 33/566* (2013.01); *C07K 2317/34* (2013.01); *C07K 2317/75* (2013.01); *G01N 2333/475* (2013.01); *G01N 2500/02* (2013.01)

(58) Field of Classification Search
None
See application file for complete search history.

(56) References Cited

U.S. PATENT DOCUMENTS

2004/0137513 A1* 7/2004 Devaux et al. ................ 435/7.1

FOREIGN PATENT DOCUMENTS

WO    0198361  A2    12/2001

OTHER PUBLICATIONS

Shelton et al., Human trks: Molecular Cloning, Tissue Distribution, and Expression of Extracellular Domain Immunoadhesins, Jan. 1995, The Journal of Neuorscience 15(1):477-491.*
International Search Report, International Application No. PCT/CA2010/001906 filed Nov. 30, 2010, pp. 1-6 (Apr. 7, 2011).
Guillemard, V. et al., An Agonistic mAb Directed to the TrkC Receptor Juxtamembrane Region Defines a Trophic Hot Spot and Interactions With p75 Coreceptors., Dev Neurobiol, Feb. 15, 2010, vol. 70, pp. 150-164, ISSN 1932-8451.
Ruiz, R. et al., Treatment With TrkC Agonist Antibodies Delays Disease Progression in Neuromuscular Degeneration (nmd) Mice., Hum Mol Genet, Jul. 1, 2005, vol. 14, pp. 1825-1837, ISSN 0964-6906.
Sahenk, Z et al., TrkB and TrkC Agonist Antibodies Improve Function, Electrophysiologic and Pathologic Features in Trembler J Mice., Exp Neurol, Aug. 2010, Epublication May 27, 2010, vol. 224, pp. 495-506, ISSN 0014-4886.

* cited by examiner

*Primary Examiner* — John Ulm
(74) *Attorney, Agent, or Firm* — Norton Rose Fulbright Canada LLP

(57) ABSTRACT

There are provided herein novel monoclonal antibodies that selectively bind and/or activate TrkC receptors, pharmaceutical compositions thereof and the use thereof for treating or preventing conditions which require activation of TrkC, such as amyotrophic lateral sclerosis and other neurodegenerative conditions and motor neuron diseases. The monoclonal antibodies are useful to screen for agents that share the same binding epitope on the TrkC receptor.

20 Claims, 8 Drawing Sheets

```
SEQUENCE LISTING

<160> NUMBER OF SEQ ID NOS: 1

<210> SEQ ID NO 1
<211> LENGTH: 18
<212> TYPE: PRT
<213> ORGANISM: Mus musculus

<400> SEQUENCE: 1

Glu Ser Thr Asp Asn Phe Ile Leu Phe Asp Glu Val Ser Pro Thr Pro
1               5                   10                  15

Pro Ile
```

AGONISTIC ANTIBODIES TO TRKC RECEPTORS AND USES THEREOF

FIELD OF THE INVENTION

This invention relates to novel monoclonal antibodies that selectively bind and activate TrkC receptors, pharmaceutical compositions thereof and use thereof for treating or preventing conditions which require activation of TrkC, such as amyotrophic lateral sclerosis, and for inhibiting neurodegeneration. Functionally active monoclonal antibodies can be used to screen for TrkC-binding agents that share the epitope on the TrkC receptor, or that allosterically interfere with the binding of the antibodies to TrkC receptor.

BACKGROUND OF THE INVENTION

Trk tyrosine kinase receptors are multi-domain single-transmembrane receptors that play an important role in a wide spectrum of neuronal responses including survival, differentiation, growth and regeneration. They are high affinity receptors for neurotrophins, a family of protein growth factors which includes nerve growth factor (NGF), brain derived neurotrophic factor (BDNF), neurotrophin-3 (NT-3) and neurotrophins-4/5 (NT-4/5). NT-3, BDNF and NGF are essential growth factors for the development and maintenance of the nervous system. The neurotrophins are stable homodimers that bind to either or both of two types of cell surface receptors termed $p75^{NTR}$ and Trk.

Mature neurotrophins bind a selective Trk receptor with relatively high affinity (e.g. TrkB-BDNF, TrkA-NGF and TrkC-NT-3). TrkC is the preferred receptor for NT-3 and mediates the multiple effects of NT-3, including neuronal death or survival, and cellular differentiation. The Trk receptor has tyrosine kinase catalytic activity that is associated with the survival and differentiation of neurotrophic signals. Neurotrophin-induced Trk activity affords trophic (growth/survival) responses via MAPK and Akt, whereas PLC-γ and fibroblast growth factor receptor substrate-2 (FRS-2) activity are involved in differentiation.

Trk receptors are widely distributed in the central nervous system and the peripheral nervous system, and play a key role in neuronal survival, differentiation and maintenance of proper function. The relevance of Trk receptor function has been demonstrated in a number of neurodegenerative models, including stroke, spinal cord injury, optic nerve axotomy, glaucoma and amyotrophic lateral sclerosis (ALS). For example, motor neurons express the TrkC receptor, and therefore agents that activate TrkC may be useful for preventing motor neuron degeneration in disorders such as ALS. In addition, Trk receptors have also been implicated in neoplasias, in particular TrkC has been associated with progression in neuroblastoma, medulloblastoma, prostate cancer, and breast cancer. In at least some of these diseases of abnormal cell proliferation, activation of Trk receptors has proven beneficial by induction of tumor death.

A Trk receptor ectodomain termed D5 comprises the main neurotrophin binding site and is required for ligand-dependent receptor activation. Such receptor sites that define ligand-binding and functional-activation are termed "hot spots". Previously, it has been demonstrated that artificial ligands, such as antibodies, that bind to a receptor hot spot could be functionally active). For example, an agonistic mAb 5C3 directed to a hot spot of the TrkA D5 domain has been reported (LeSauteur et al., 1996, J. Neurosci. 16: 1308-1316).

All mature neurotrophins also bind to $p75^{NTR}$, while the precursor pro-neurotrophins bind $p75^{NTR}$ exclusively and do not bind Trk receptors. It is known that the $p75^{NTR}$ receptor can affect Trk-binding or function, although the mechanism is not fully understood. It has been shown that $p75^{NTR}$ can unmask a cryptic "hot spot" of Trk receptors, suggesting the notion of allosteric regulation.

ALS is a progressive, fatal, neurodegenerative disease caused by the degeneration of motor neurons, the nerve cells in the central nervous system that control voluntary muscle movement. The disorder causes muscle weakness and atrophy throughout the body as both the upper and lower motor neurons degenerate, unable to send messages to the muscles which then degenerate and atrophy due to their inability to function. ALS is one of the most common neuromuscular diseases worldwide, with one or two out of 100,000 people developing ALS each year. The disease most commonly strikes people between 40 and 60 years of age. ALS is fatal, usually within 3 to 5 years of the onset of symptoms.

Current and prospective treatments for ALS are focused on neuroprotective agents. One of the few available treatments is the neuroprotective agent Riluzole, which is believed to reduce damage to motor neurons by decreasing the release of glutamate, and has been shown to lengthen patient survival by several months. There is presently no cure for ALS. There is a need therefore for new and effective therapies to prevent, inhibit or treat ALS.

SUMMARY OF THE INVENTION

The present invention relates to novel agonistic anti-TrkC monoclonal antibodies (mAbs), pharmaceutical compositions thereof, and use thereof for diagnosing, treating, or preventing conditions (including symptoms, disorders, or diseases) which require activation of TrkC, such as diseases involving neurodegeneration and motor neuron diseases such as amyotrophic lateral sclerosis (ALS).

In accordance with one embodiment of the present invention, there are provided monoclonal antibodies that specifically bind the juxtamembrane domain of the TrkC receptor, or a peptide sequence within the juxtamembrane domain of TrkC. Fragments, portions, variants or derivatives of the monoclonal antibodies which retain the binding specificity or agonist activity of the full-length antibodies are also provided herein. In an embodiment, the antibodies provided herein specifically bind and/or activate TrkC.

In another embodiment, the antibodies provided herein can activate TrkC, i.e. can act as agonists of the TrkC receptor. In one aspect, the antibodies provided herein are specific for TrkC and do not bind and/or activate TrkA, TrkB and/or p75NTR receptors. In a further aspect, the antibodies provided herein bind or activate TrkC differently from NT-3. The TrkC may be any mammalian TrkC, including but not limited to human TrkC, murine TrkC and rat TrkC.

As used herein, the term "differently from" in relation to binding or activation refers to binding to a different binding site or binding differently to a site (e.g. binding more strongly), and/or having a different effect once bound (e.g. different activation properties, causing different biological consequences, and so on). For example, the 2B7 antibody binds to a different binding site on TrkC than the natural ligand NT-3 (e.g. juxtamembrane domain rather than D5 domain), the 2B7 antibody causes activation of some but not all of the TrkC signaling pathways that NT-3 can activate (e.g. phospho-AKT is efficiently activated but phospho-MAPK is only poorly activated), and 2B7 causes some but not all of the biological consequences that NT-3 can cause (e.g. neuronal survival but not neuronal differentiation). The expression of p75NTR also regulates 2B7 binding and activity on TrkC differently from that of NT-3, as 2B7 binding and efficacy is reduced by p75NTR, whereas NT-3 binding is enhanced by p75NTR. Thus binding or activating "differently" refers to any difference in binding and/or activation properties or any combination of these properties.

In yet another embodiment, the antibodies provided herein specifically bind an epitope of TrkC with a sequence comprising the juxtamembrane domain of TrkC. In an embodiment, the antibodies provided herein specifically bind an epitope of TrkC located between the transmembrane domain and the D5 domain. In another embodiment, the antibodies provided herein bind selectively to native TrkC on the cell surface, near the juxtamembrane region, and do not bind to p75, TrkB, or TrkA. The TrkC may be any mammalian TrkC, including but not limited to human TrkC, murine TrkC and rat TrkC.

There is also provided herein a monoclonal antibody that is produced from the hybridoma deposited under the Budapest Treaty with the International Depositary Authority of Canada on May 26, 2010 and having accession no. 090314-02 or from a progenitor cell thereof. In another aspect, antibodies (or fragments, portions, variants or derivatives thereof) binding to the same epitope as the monoclonal antibody produced from the hybridoma deposited with the International Depositary Authority of Canada on May 26, 2010 and having accession no. 090310-02 are provided. The antibodies of the invention may be humanized or modified in any way which provides benefit without altering the binding properties or the biological activity of the antibodies. Non-limiting examples of fragments, portions, variants or derivatives of the antibodies include single chain antibodies and Fab fragments thereof. A hybridoma that produces a monoclonal antibody according to the invention is also encompassed herein.

There is further provided herein an antibody which comprises complementarity-determining regions (CDRs) and/or hypervariable domains of an antibody produced by a hybridoma having IDAC patent deposit designation 090310-02.

In a further embodiment, pharmaceutical compositions comprising the antibodies of the invention or the fragments, portions, variants or derivatives thereof, and a pharmaceutically acceptable carrier, are provided.

In accordance with another embodiment of the invention, there is provided a method of activating TrkC in a subject, comprising administering a therapeutically effective amount of a monoclonal antibody of the invention or a fragment, portion, variant or derivative thereof to the subject, such that TrkC is activated in the subject. In an aspect, the subject is human and the TrkC is human TrkC. In another aspect, the subject suffers from a neurological or neurodegenerative condition which requires activation of TrkC. For example, the subject may have been injured by a wound, surgery, ischemia, infection, a metabolic disease, malnutrition, a malignant tumor or a toxic drug, or may have suffered a stroke, spinal cord injury or an axotomy. In one aspect, the subject suffers from a neurodegenerative disease which is amyotrophic lateral sclerosis (ALS). In an aspect, the subject suffers from a motor neuron disease.

In an aspect, the antibodies of the invention may be administered to a subject parenterally, intravenously, subcutaneously or interperitoneally. In another aspect, the antibodies of the invention may be administered in combination with a second therapeutic agent, such as an agent for treating ALS.

In other embodiments, methods for treating ALS or for treating or preventing a neurodegenerative condition or a motor neuron disease in a subject, comprising administering a therapeutically effective amount of a monoclonal antibody of the invention, or a fragment, portion, variant or derivative thereof, are provided.

In further embodiments, fragments, portions, variants or derivatives of the monoclonal antibody produced by the hybridoma having IDAC patent deposit designation 090310-02, said fragments, portions, variants or derivatives binding specifically to the same epitope as the monoclonal antibody, are provided herein. The monoclonal antibody produced by the hybridoma having IDAC patent deposit designation 090310-02 or antigen-binding fragments, portions, variants or derivatives thereof may also be humanized, veneered, or chimeric.

In some embodiments, the monoclonal antibody produced by the hybridoma having IDAC patent deposit designation 090310-02 or antigen-binding fragments, portions, variants or derivatives thereof specifically bind TrkC receptor, or may specifically bind TrkC receptor juxtamembrane domain, or the region between the transmembrane domain and the D5 domain. In additional embodiments, the monoclonal antibody produced by the hybridoma having IDAC patent deposit designation 090310-02 or antigen-binding fragments, portions, variants or derivatives thereof activate TrkC receptor.

There are also provided herein methods of in vitro screening for an agent which binds to TrkC receptor and can thereby affect TrkC receptor biological activity, comprising combining the antibodies or the fragments, portions, variants or derivatives of the invention with TrkC receptor, in the presence or absence of a candidate agent, and determining whether binding of the antibodies to TrkC receptor or to a fragment or peptide thereof is reduced in the presence of the candidate agent, wherein a reduction in antibody binding in the presence of the candidate agent indicates that said candidate agent binds directly to, or allosterically alters TrkC, and can thereby modulate TrkC receptor biological activity.

BRIEF DESCRIPTION OF THE DRAWINGS

Particular embodiments of the present invention will now be explained by way of example and with reference to the accompanying drawings, in which.

DETAILED DESCRIPTION OF THE INVENTION

Figure 1:
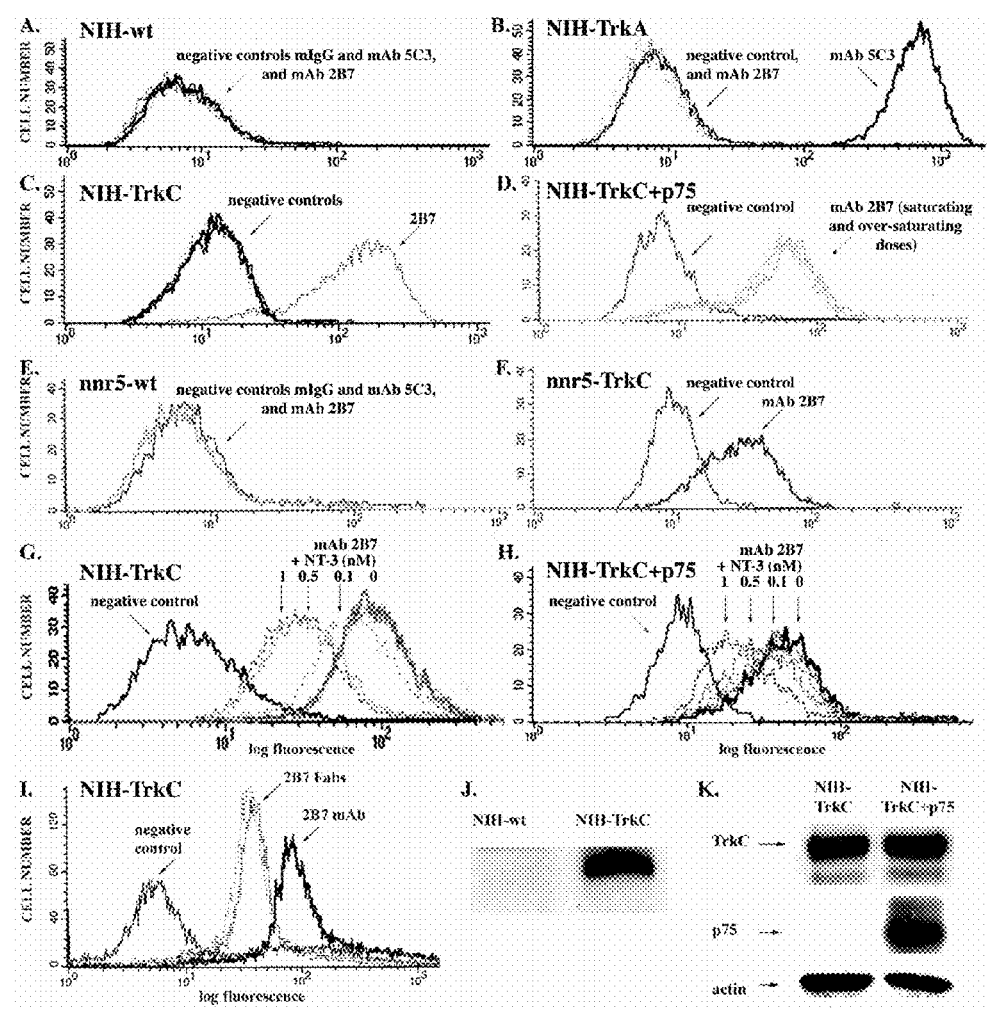
FIG. 1 shows that mAb 2B7 binds selectively to TrkC receptor expressing cells. All data are representative of at least three independent assays. (A-F) show FACScan binding assays with mAb 2B7. The indicated cells were incubated with a saturating concentration of mAb 2B7 (~65 nM or higher). (G, H) show dose-dependent competition of mAb 2B7 binding by NT-3. NIH-TrkC or NIH-TrkC$^+$p75 cells were studied. Note reduced mAb 2B7 immunofluorescence in NIH-TrkC$^+$p75 cells although they express the same levels of TrkC (see panel K). These data suggest modulation of the 2B7 TrkC-binding site, which is likely allosteric. (I) shows comparable FACScan saturability profiles in NIH TrkC cells for mAb 2B7 and 2B7 Fabs. (J) shows that 2B7 recognizes TrkC in Western blots, under non-reducing conditions. (K) shows that total levels of TrkC receptor are similar in NIH-TrkC and NIH-TrkC$^+$p75 cells. NIH-TrkC$^+$p75 cells express high levels of p75. It is noted that the doublet seen for TrkC may be differentially glycosylated receptor.

The present invention provides monoclonal antibodies (mAbs) that selectively target TrkC. Agonist monoclonal antibodies that activate TrkC, pharmaceutical compositions thereof, and use thereof for treating diseases involving neurodegeneration and/or for providing neuroprotection, including motor neuron diseases such as amyotrophic lateral sclerosis (ALS), are provided herein.

The present invention is based, at least in part, on the principle that monoclonal antibodies that specifically bind to the TrkC receptor are sufficient to induce the activation of the receptor, and therefore induce biological responses similar to those mediated by, for example, NT-3. Monoclonal antibodies such as those provided herein can act as agonists that mimic the biological effects of receptor-ligand interactions.

There is provided herein a monoclonal antibody (mAb) 2B7 targeting the juxtamembrane domain of TrkC receptors. MAb 2B7 binds to murine and human TrkC receptors and is a functional agonist that affords activation of TrkC, AKT and MAPK. These signals result in cell survival but not in cellular differentiation. Monomeric 2B7 Fabs also afford cell survival. Binding of 2B7 mAb and 2B7 Fabs to TrkC are blocked by NT-3 in a dose-dependent manner, but not by pro-NT-3. Expression of p75$^{NTR}$ co-receptors on the cell surface block the binding and function of mAb 2B7, whereas NT-3 binding and function are enhanced. MAb 2B7 defines a previously unknown neurotrophin receptor functional hot spot. The antibody exclusively generates survival signals and can be activated by non-dimeric ligands.

The hot spot defined by MAb 2B7, and other "hot spots" on Trk receptors, should allow different modes of activation for the receptors. Agents that bind at such hot spots and modulate receptor activity might be useful for treating disorders such as neurodegeneration or cancer. Agents that bind at such hot spots and modulate receptor activity might also be useful as a tool to screen for agents that also bind to the same hot spots.

In one aspect, the present invention provides monoclonal antibodies that bind specifically to TrkC. In certain embodiments the antibodies bind to human TrkC. In another embodiment the antibodies bind to rat and/or mouse TrkC. In certain embodiments, the antibodies bind preferentially to human TrkC, and do not bind to TrkA, TrkB and/or p75NTR receptors.

In one embodiment the antibodies provided herein are also agonists of TrkC.

In another embodiment the antibodies provided herein bind to the ESTDNFILFDEVSPTPPI (SEQ ID NO: 1) peptide, which is near the D5 domain. In an embodiment, the receptor site for antibody binding is located between the transmembrane domain and the D5 domain of TrkC. In another embodiment, the receptor site for antibody binding is located in the extracellular domain of TrkC. In one embodiment, the antibodies of the invention bind selectively to native TrkC on the cell surface, near the juxtamembrane region, and do not bind to p75, TrkB, or TrkA. In another aspect, the present invention provides any monoclonal antibodies with the properties described herein that bind and/or activate human, rat or mouse TrkC.

In certain embodiments, these antibodies bind and/or activate TrkC with an ED50 in the range of about 10 pM to about 500 nM, for example in the range of about 10 pM to about 1 nM, including in the range of about 10 pM to about 500 pM and the range of about 10 pM to about 100 pM.

In another aspect, the present invention provides monoclonal antibodies with any of the properties described herein that bind one or more specific epitopes near the juxtamembrane region of human TrkC. In yet another aspect, the present invention provides monoclonal antibodies with any of the properties described herein that bind specifically to the region between the transmembrane domain and the D5 domain of human, rat or mouse TrkC.

In yet another aspect, the present invention provides hybridomas that produce any of the monoclonal antibodies of the invention. For example, the hybridoma that was deposited with the International Depositary Authority of Canada on May 26, 2010 and given accession no. 090310-02 is provided. In still another aspect, the present invention provides the monoclonal antibody produced by the hybridoma that was deposited with the IDAC on May 26, 2010 and given accession no. 090310-02, or antigen-binding fragments thereof. The present invention also provides antibodies that block the binding of this antibody and therefore share the same binding epitope on human, rat or mouse TrkC.

It is to be understood that the monoclonal antibodies of the invention can be prepared by any known method. For example, they can be prepared using synthetic, recombinant or hybridoma technology (e.g., as described in Antibodies: A Laboratory Manual, Ed. by E. Harlow and D. Lane, Cold Spring Harbor Laboratory Press, 1988 or Monoclonal Antibodies: Principles and Practice by J. W. Goding, Academic Press, 1996). In particular it will be appreciated that the antibodies provided herein can be prepared by initially immunizing an animal with human TrkC or a derivative thereof (e.g., a recombinant protein that includes the desired domain of human TrkC, such as recombinant human TrkC juxtamembrane region) and then preparing monoclonals from suitably prepared hybridomas. Those skilled in the art will appreciate that suitable immunogens can be prepared using standard recombinant technology (e.g., see Protocols in Molecular Biology Ed. by Ausubel et al., John Wiley & Sons, New York, N.Y., 1989 and Molecular Cloning: A Laboratory Manual Ed. by Sambrook et al., Cold Spring Harbor Press, Plainview, N.Y., 1989, the contents of which are incorporated herein by reference).

In certain embodiments, the immunogen used does not include any of the amino acids that are found in the intracellular domain of TrkC or in the D5 domain of TrkC. Once suitable immunogens have been prepared, the immunogens are injected into any of a wide variety of animals (e.g., mice, rats, rabbits, etc.) and antibodies are prepared using standard, art-recognized techniques.

When using the antibodies provided herein for therapeutic purposes it may prove advantageous to use a humanized or veneered version of the antibody of interest to reduce any potential immunogenic reaction. In general, humanized or veneered antibodies minimize unwanted immunological responses that limit the duration and effectiveness of therapeutic applications of non-human antibodies in human recipients.

A number of methods for preparing humanized antibodies comprising an antigen binding portion derived from a non-human antibody have been described in the art. In particular, antibodies with rodent variable regions and their associated complementarity-determining regions (CDRs) fused to human constant domains have been described, as have rodent CDRs grafted into a human supporting framework region (FR) prior to fusion with an appropriate human antibody constant domain. Completely human antibodies are particularly desirable for therapeutic treatment of human patients. Such antibodies can be produced using transgenic mice that are incapable of expressing endogenous immunoglobulin heavy and light chain genes, but which can express human heavy and light chain genes. It should be understood that partially or completely humanized versions of the antibodies provided herein are encompassed by the present invention.

Veneered versions of the antibodies provided herein may also be used in the methods of the present invention. The process of veneering involves selectively replacing FR residues from, e.g., a murine heavy or light chain variable region, with human FR residues in order to provide an antibody that comprises an antigen binding portion which retains substantially all of the native FR protein folding structure. Veneering techniques are based on the understanding that the antigen binding characteristics of an antigen binding portion are determined primarily by the structure and relative disposition of the heavy and light chain CDR sets within the antigen-association surface (e.g., see Davies et al., Ann. Rev. Biochem. 59:439, 1990). Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface. It should be understood that veneered versions of the antibodies provided herein are encompassed by the present invention.

The term "antibody", as used herein, broadly refers to any immunoglobulin (Ig) molecule comprised of four polypeptide chains, two heavy (H) chains and two light (L) chains, or any functional fragment, mutant, variant, or derivative thereof, which retains the essential epitope binding features of an Ig molecule. Such mutant, variant, or derivative antibody formats are known in the art. A "monoclonal antibody" as used herein is intended to refer to a preparation of antibody molecules, which share a common heavy chain and common light chain amino acid sequence, in contrast with "polyclonal" antibody preparations that contain a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature256:495-497).

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen-binding portion" or "antigen-binding fragment" of an antibody (or simply "antibody portion" or "antibody fragment"), as used herein, refers to one or more fragments of an antibody that retain the ability to specifically bind to an antigen (e.g., juxtamembrane region domain of TrkC). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1, herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the present invention. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

It should be understood that the antibodies of the invention include fragments, portions, variants or derivatives thereof, such as single-chain antibodies or Fab fragments, that retain the same binding properties (e.g. specificity or affinity) of the full-length antibodies.

The antibodies of the invention also include functional equivalents that include polypeptides with amino acid sequences substantially the same as the amino acid sequence of the variable or hypervariable regions of the antibodies of the present invention. "Substantially the same" amino acid sequence includes an amino acid sequence with at least 70%, preferably at least 80%, and more preferably at least 90% identity to another amino acid sequence when the amino acids of the two sequences are optimally aligned and compared to determine exact matches of amino acids between the two sequences. "Substantially the same" amino acid sequence also includes an amino acid sequence with at least 70%, preferably at least 80%, and more preferably at least 90% homology to another amino acid sequence, as determined by the FASTA search method in accordance with Pearson and Lipman, Proc. Natl. Acad. Sci. USA 85, 2444-8 (1988).

In addition, proteins and non-protein agents may be conjugated to the antibodies by methods that are known in the art. Conjugation methods include direct linkage, linkage via covalently attached linkers, and specific binding pair members (e.g., avidin-biotin). For example, an antibody of the invention may include modifications that retain specificity for juxtamembrane region of TrkC. Such modifications include, but are not limited to, conjugation to an effector molecule such as another therapeutic agent or conjugation to detectable reporter moieties. For example conjugation of a therapeutic agent to an antibody of the invention may be used to deliver the therapeutic agent, e.g. a drug or pro-drug, to a cell via the TrkC receptor. Many anti-cancer therapeutics are known in the art, and it is contemplated that such therapeutics, for example, may be conjugated to an antibody of the invention for TrkC-mediated delivery in a subject. Modifications that extend antibody half-life (e.g., pegylation) are also included.

In certain embodiments, the antibodies presented herein are characterized for their binding activities to human TrkC protein (e.g., using ELISA, FACS, Surface Plasmon Resonance, and/or other methods known in the art). In certain embodiments binding to human TrkC proteins that are expressed on a cell surface may also be assessed (e.g., using cell lines, as known in the art), as well as determination of functional properties using said cell lines. Antibodies may also be tested for their cross-species binding activity; this allows monoclonal antibodies that bind TrkC from more than one species to be identified. In an embodiment, the mAbs bind to both human TrkC and rat TrkC. These antibodies are of interest since they can be tested in animal models with the knowledge that they can also be applied in human clinical trials.

In certain embodiments it may prove advantageous to further characterize the binding properties of any given monoclonal antibody. In particular, one may use a competition assay (e.g., an ELISA) to determine whether the antibodies block the interaction of TrkC and NT-3. One may also assess whether the antibodies bind non-human TrkC and/or human TrkA, TrkB or p75NTR. Mapping of the relative antibody binding epitopes on TrkC (human or other) may also be conducted, e.g., by examining the activity of each individual antibody in blocking the binding of other antibodies to TrkC. For example, the observation that two antibodies block each other's binding suggests these antibodies may bind to the same epitope or overlapping epitopes on TrkC. Methods for mapping epitopes are well-known in the art.

In certain embodiments, the antibodies presented herein are characterized for their functional ability to activate TrkC which may be human or non-human TrkC (e.g. murine, rat, chicken, etc). Any agonist assay may be used. For example, MTT-based survival/proliferation assays in cell lines may be used. These assays and other useful assays are known in the art and will be recognized by those skilled in the art.

Pharmaceutical Compositions

In one aspect, the monoclonal antibodies provided herein are administered to a subject in order to activate TrkC, in accordance with the present invention. In another aspect, the monoclonal antibodies provided herein are administered in the context of a pharmaceutical composition, that contains a therapeutically effective amount of one or more antibodies together with one or more other ingredients known to those skilled in the art for formulating pharmaceutical compositions. As used herein, the terms "pharmaceutically effective amount" or "therapeutically effective amount" mean the total amount of each active ingredient of the pharmaceutical composition or method that is sufficient to show a meaningful patient benefit, e.g., treatment, prevention or amelioration of a condition which requires TrkC activation. When applied to an individual active ingredient that is administered alone, the term refers to that ingredient alone. When applied to a combination of active ingredients, the term refers to combined amounts of the active ingredients that result in the therapeutic effect, whether administered in combination, serially or simultaneously.

In certain embodiments of the invention, inventive antibodies are administered with a weekly dose in the range of about 0.1 to about 1000 mg/kg body weight, or about 1 to about 500 mg/kg body weight, in certain embodiments about 10 to about 300 mg/kg body weight. Doses may be administered as a single regimen or as a continuous regimen divided by two or more doses over the course of a day or week. Delivery may be as a bolus or in certain embodiments as a gradual infusion (e.g., by injection over 30 mins) or as a continuous infusion (e.g. days) using minipumps, or using slow release delivery particles or cells that have been engineered to secrete the inventive antibodies. In certain embodiments one or more higher doses (e.g., 2, 3 or 4 fold higher) may be administered initially followed by one or more, lower maintenance doses. The higher dose(s) may be administered at the onset of treatment only or at the beginning of each treatment cycle. These dosage levels and other dosage levels herein are for intravenous or intraperitoneal administration. The skilled person will readily be able to determine the dosage levels required for a different route of administration. It will be appreciated that, in general, the precise dose used will be as determined by the prescribing physician and will depend not only on the weight of the subject and the route of administration, but also on the age of the subject and the severity of the symptoms.

Additional ingredients useful in preparing pharmaceutical compositions in accordance with the present invention include, for example, carriers (e.g., in liquid or solid form), flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof. Liquid pharmaceutical compositions preferably contain one or more monoclonal antibodies of the invention and one or more liquid carriers to form solutions, suspensions, emulsions, syrups, elixirs, or pressurized compositions. Pharmaceutically acceptable liquid carriers include, for example water, organic solvents, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof. If the liquid formulation is intended for pediatric use, it is generally desirable to avoid inclusion of alcohol.

Examples of liquid carriers suitable for oral or parenteral administration include water (preferably containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Solid pharmaceutical compositions preferably contain one or more solid carriers, and optionally one or more other additives such as flavoring agents, lubricants, solubilizers, suspending agents, fillers, glidants, compression aids, binders or tablet-disintegrating agents or an encapsulating material. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier is preferably a finely divided solid which is in admixture with the finely divided active ingredient. In tablets, the active ingredient(s) are generally mixed with a carrier having the necessary compression properties in suitable proportions, and optionally, other additives, and compacted into the desired shape and size.

In some embodiments of the invention, pharmaceutical compositions are provided in unit dosage form, such as tablets or capsules. In such form, the composition is sub-divided in unit dose containing appropriate quantities of the active ingredient(s). The unit dosage forms can be packaged compositions, for example packeted powders, vials, ampoules, pre-filled syringes or sachets containing liquids. The unit dosage form can be, for example, a capsule or tablet itself, or it can be an appropriate number of any such compositions in package form. Thus, the present invention also provides a pharmaceutical composition in unit dosage form for activating TrkC, where the composition contains a therapeutically effective unit dosage of at least one monoclonal antibody of the invention. As one skilled in the art will recognize, the certain therapeutically effective unit dosage will depend on the method of administration. The present invention also provides a therapeutic package for dispensing the monoclonal antibodies of the invention to an individual being treated for a condition which requires TrkC activation. In some embodiments, the therapeutic package contains one or more unit dosages of at least one inventive monoclonal antibody, a container containing the one or more unit dosages, and labeling directing the use of the package for treatment. In certain embodiments, the unit dose is in tablet or capsule form. In some cases, each unit dosage is a therapeutically effective amount.

According to the present invention, monoclonal antibodies of the invention may be administered alone to modulate TrkC activity. Alternatively the antibodies may be administered in combination with (whether simultaneously or sequentially) one or more other pharmaceutical agents useful in the treatment, prevention or amelioration of one or more other conditions (including symptoms, disorders, or diseases) which require TrkC activity. For example, other pharmaceutical agents that can modulate TrkC activity may be used in combination with the monoclonal antibodies of the invention, including other activators of TrkC, including but not limited to NT-3 derivatives and compositions.

Additionally or alternatively, the monoclonal antibodies may be used in conjunction with other pharmaceutical agents that are useful in the treatment, prevention or amelioration of neurological disorders and diseases or of motor neuron disorders and diseases. In certain embodiments, the monoclonal antibodies are combined with agents that are useful in the treatment, prevention or amelioration of disorders and diseases caused by injuries to the nervous system (e.g., by wound, surgery, ischemia, infection, metabolic diseases, malnutrition, malignant tumor, toxic drugs, etc.), particularly to the motor neurons. It is to be understood that any suitable agent known in the art may be used, including those listed in the Physicians' Desk Reference, $55^{th}$ Edition, 2001, published by Medical Economics Company, Inc. at Monvale, N.J., the relevant portions of which are incorporated herein by reference.

Currently the only prescribed drug approved by the U.S. Food and Drug Administration to treat ALS is the drug riluzole (Rilutek®), which prolongs life by 2-3 months but does not relieve symptoms. The drug reduces the body's natural production of the neurotransmitter glutamate, which carries signals to the motor neurons. Scientists believe that too much glutamate can harm motor neurons and inhibit nerve signaling.

Other treatments are symptomatic. Muscle relaxants such as baclofen, tizanidine, and the benzodiazepines may reduce spasticity. Glycopyrrolate and atropine may reduce the flow of saliva. Quinine or phenyloin may decrease cramps. Anticonvulsants and nonsteroidal anti-inflammatory drugs may help relieve pain, and other drugs can be prescribed to treat depression. Tranquilizers often help with sleeping problems. Some individuals with PPS develop sleep apnea (a potentially life-threatening condition characterized by interruptions of breathing during sleep), which can be treated with decongestant therapy, assisted breathing at night, or surgery to remove any blockage to the airway. Panic attacks over fears of choking to death can be treated with benzodiazepines. Botulinum toxin may be used to treat jaw spasms or drooling. Amitriptyline and other drugs can help control excess drooling. Some individuals may eventually require stronger medicines such as morphine to cope with musculoskeletal abnormalities or pain, and opiates are used to provide comfort care in terminal stages of the disease.

In one embodiment, the monoclonal antibodies may be used in conjunction with riluzole and/or with symptomatic treatments for motor neuron diseases, such as for example muscle relaxants, tranquilizers, anticonvulsants, nonsteroidal anti-inflammatory drugs, benzodiazepines and amitriptyline.

In the therapeutic methods provided herein, the monoclonal antibodies may be delivered to a subject using any appropriate route of administration including, for example, parenteral, intravenous, topical, nasal, oral (including buccal or sublingual), rectal or other modes. In general, the antibodies may be formulated for immediate, delayed, modified, sustained, pulsed, or controlled-release delivery.

In certain embodiments, the antibodies are formulated for delivery by injection. In such embodiments, administration may be, for example, intracavernous, intravenous, intra-arterial, intraperitoneal, intrathecal, intraventricular, intraurethral, intrasternal, intracranial, intramuscular or subcutaneous, or via infusion or needle-less injection techniques. For such parenteral administration, the antibodies of the invention may be prepared and maintained in conventional lyophilized formulations and reconstituted prior to administration with a pharmaceutically acceptable saline solution, such as a 0.9% saline solution. The pH of the injectable formulation can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the inventive antibody, it may be desirable to slow its absorption from an intramuscular or subcutaneous injection. Delayed absorption of such an administered antibody may be accomplished by dissolving or suspending the agent in an oil vehicle. Injectable depot forms are made by forming microencapsule matrices of the antibody in biodegradable polymers such as polylactide-polyglycolide. Depending upon the ratio of antibody to polymer and the nature of the particular polymer employed, the rate of antibody release can be controlled. Examples of other biodegradable polymers include poly(orthoesters) and poly(anhydrides). Depot injectable formulations are also prepared by entrapping the antibodies in liposomes or microemulsions which are compatible with body tissues.

For application topically to the skin, the antibodies can be formulated as a suitable ointment containing the active ingredient suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following mineral oil, sorbitan monostearate, a polyethylene glycol, liquid paraffin, polysorbate 60, cetyl esters wax, cetearyl alcohol, 2-octyldodecanol, benzyl alcohol and water. The inventive antibodies can also be administered intranasally or by inhalation and are conveniently delivered in the form of a dry powder inhaler or an aerosol spray presentation from a pressurized container, pump, spray, atomiser or nebuliser, with or without the use of a suitable propellant, e.g. dichlorodifluoromethane, trichlorofluoromethane, dichlorotetrafluoroethane, a hydrofluoroalkane, carbon dioxide or other suitable gas. In the case of a pressurized aerosol, the dosage unit may be determined by providing a valve to deliver a metered amount. The pressurized container, pump, spray, atomiser or nebuliser may contain a solution or suspension of the antibody, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of the antibodies of the invention and a suitable powder base such as lactose or starch.

For oral delivery, such delivery may be accomplished using solid or liquid formulations, for example in the form of tablets, capsules, multiparticulates, gels, films, ovules, elixirs, solutions or suspensions. In certain embodiments, the monoclonal antibodies are administered as oral tablets or capsules. Such preparations may be mixed chewable or liquid formulations or food materials or liquids if desirable, for example to facilitate administration to children, to individuals whose ability to swallow tablets is compromised, or to animals. Compositions for rectal administration are preferably suppositories which can be prepared by mixing the inventive antibodies with suitable non-irritating excipients or carriers such as cocoa butter, polyethylene glycol or a suppository wax which are solid at ambient temperature but liquid at body temperature and therefore melt in the rectal vault and release the antibodies. Retention enemas and rectal catheters can also be used as is known in the art. Viscosity-enhancing carriers such as hydroxypropyl cellulose are also certain carriers of the invention for rectal administration since they facilitate retention of the pharmaceutical composition within the rectum. Generally, the volume of carrier that is added to the pharmaceutical composition is selected in order to maximize retention of the composition. In particular, the volume should not be so large as to jeopardize retention of the administered composition in the rectal vault.

Therapeutic Uses

In one aspect, inventive antibodies and compositions are useful for treating or preventing conditions (including symptoms, disorders, or diseases) which require activation of TrkC. Such methods involve administering a therapeutically effective amount of one or more of the antibodies provided herein to a subject. In certain embodiments, the invention provides methods for treating neurological conditions, neurodegenerative diseases and/or for providing neuroprotection, and/or for treating motor neuron diseases, and/or for diagnosing a condition such as cancer.

For example, and without limitation, the antibodies provided herein may be used to treat individuals with a nervous system that has been injured by wound, surgery, ischemia, infection, metabolic diseases, malnutrition, malignant tumor, toxic drug, etc. Specific examples include stroke, spinal cord injury, traumatic brain injury, retinal degeneration and axotomy. The inventive antibodies may also be used to treat disorders such as attention-deficit hyperactivity disorder (ADHD), depression and age-associated mental impairment (i.e., by providing cognitive enhancement). The inventive antibodies and compositions may also be used to treat congenital or neurodegenerative conditions including Alzheimer's disease, Parkinson's disease, Huntington's chorea, amyotrophic lateral sclerosis (ALS) and conditions related to these.

In one embodiment, inventive antibodies and compositions are useful for treating or preventing motor neuron diseases. Motor neurons express the TrkC receptor and are dependent on NT-3. Motor neuron diseases are a group of progressive neurological disorders that destroy motor neurons, the cells that control essential voluntary muscle activity such as speaking, walking, breathing, and swallowing. Normally, messages from nerve cells in the brain (called upper motor neurons) are transmitted to nerve cells in the brain stem and spinal cord (called lower motor neurons) and from them to particular muscles. Upper motor neurons direct the lower motor neurons to produce movements such as walking or chewing. Lower motor neurons control movement in the arms, legs, chest, face, throat, and tongue. When there are disruptions in these signals, the muscles do not work properly; the result can be gradual weakening, wasting away, and uncontrollable twitching (called fasciculations). When upper motor neurons are affected, the manifestations include spasticity or stiffness of limb muscles and over-activity of tendon reflexes such as knee and ankle jerks. Eventually, the ability to control voluntary movement can be lost. Motor neuron diseases may be inherited or sporadic.

Many motor neuron diseases are known. Common motor neuron diseases include amyotrophic lateral sclerosis (ALS), which affects both upper and lower motor neurons. Progressive bulbar palsy affects the lower motor neurons of the brain stem, causing slurred speech and difficulty chewing and swallowing. Primary lateral sclerosis is a disease of the upper motor neurons, while progressive muscular atrophy affects only lower motor neurons in the spinal cord.

Amyotrophic lateral sclerosis (ALS), also called Lou Gehrig's disease or classical motor neuron disease, is a progressive, ultimately fatal disorder that eventually disrupts signals to all voluntary muscles. In the United States, doctors use the terms motor neuron disease and ALS interchangeably. Both upper and lower motor neurons are affected. Approximately 75 percent of people with classic ALS will also develop weakness and wasting of the bulbar muscles (muscles that control speech, swallowing, and chewing). Other symptoms include spasticity, exaggerated reflexes, muscle cramps, fasciculations, and increased problems with swallowing and speaking. When muscles of the diaphragm and chest wall fail to function properly, individuals lose the ability to breathe without mechanical support. Although the disease does not usually impair a person's mind or personality, several recent studies suggest that some people with ALS may have alterations in cognitive functions such as problems with decision-making and memory. ALS most commonly strikes people between 40 and 60 years of age, but younger and older people also can develop the disease. Men are affected more often than women. Most cases of ALS occur sporadically, and family members of those individuals are not considered to be at increased risk for developing the disease, although there is a familial form of ALS in adults, which often results from mutation of the superoxide dismutase gene, or SOD1, located on chromosome 21. A rare juvenile-onset form of ALS is genetic. Most individuals with ALS die from respiratory failure, usually within 3 to 5 years from the onset of symptoms. However, about 10 percent of affected individuals survive for 10 or more years.

Progressive bulbar palsy, also called progressive bulbar atrophy, involves the bulb-shaped brain stem—the region that controls lower motor neurons needed for swallowing, speaking, chewing, and other functions. Symptoms include pharyngeal muscle weakness (involved with swallowing), weak jaw and facial muscles, progressive loss of speech, and tongue muscle atrophy. Limb weakness with both lower and upper motor neuron signs is almost always evident but less prominent. Affected persons have outbursts of laughing or crying (called emotional lability). Individuals eventually become unable to eat or speak and are at increased risk of choking and aspiration pneumonia, which is caused by the passage of liquids and food through the vocal folds and into the lower airways and lungs.

Pseudobulbar palsy, which shares many symptoms of progressive bulbar palsy, is characterized by upper motor neuron degeneration and progressive loss of the ability to speak, chew, and swallow. Progressive weakness in facial muscles leads to an expressionless face. Individuals may develop a gravelly voice and an increased gag reflex. The tongue may become immobile and unable to protrude from the mouth. Individuals may also experience emotional lability.

Primary lateral sclerosis (PLS) affects only upper motor neurons and is nearly twice as common in men as in women. Onset generally occurs after age 50. PLS occurs when specific nerve cells in the cerebral cortex (the thin layer of cells covering the brain which is responsible for most higher level mental functions) that control voluntary movement gradually degenerate, causing the muscles under their control to weaken. The syndrome—which scientists believe is only rarely hereditary—progresses gradually over years or decades, leading to stiffness and clumsiness of the affected muscles. The disorder usually affects the legs first, followed by the body trunk, arms and hands, and, finally, the bulbar muscles. Symptoms may include difficulty with balance, weakness and stiffness in the legs, clumsiness, spasticity in the legs which produces slowness and stiffness of movement, dragging of the feet (leading to an inability to walk), and facial involvement resulting in dysarthria (poorly articulated speech). Major differences between ALS and PLS (considered a variant of ALS) are the motor neurons involved and the rate of disease progression. PLS may be mistaken for spastic paraplegia, a hereditary disorder of the upper motor neurons that causes spasticity in the legs and usually starts in adolescence. PLS often develops into ALS.

Progressive muscular atrophy is marked by slow but progressive degeneration of only the lower motor neurons. Weakness is typically seen first in the hands and then spreads into the lower body, where it can be severe. Other symptoms may include muscle wasting, clumsy hand movements, fasciculations, and muscle cramps. The trunk muscles and respiration may become affected. Exposure to cold can worsen symptoms. The disease develops into ALS in many instances.

Spinal muscular atrophy (SMA) is a hereditary disease affecting the lower motor neurons. Weakness and wasting of the skeletal muscles is caused by progressive degeneration of the anterior horn cells of the spinal cord. This weakness is often more severe in the legs than in the arms. SMA has various forms, with different ages of onset, patterns of inheritance, and severity and progression of symptoms. Some of the more common SMAs are described below.

SMA type I, also called Werdnig-Hoffmann disease, is evident by the time a child is 6 months old. Symptoms may include hypotonia (severely reduced muscle tone), diminished limb movements, lack of tendon reflexes, fasciculations, tremors, swallowing and feeding difficulties, and impaired breathing. Some children also develop scoliosis (curvature of the spine) or other skeletal abnormalities. Affected children never sit or stand and the vast majority usually die of respiratory failure before the age of 2.

Symptoms of SMA type II usually begin after the child is 6 months of age. Features may include inability to stand or walk, respiratory problems, hypotonia, decreased or absent tendon reflexes, and fasciculations. These children may learn to sit but do not stand. Life expectancy varies, and some individuals live into adolescence or later.

Symptoms of SMA type III (Kugelberg-Welander disease) appear between 2 and 17 years of age and include abnormal gait; difficulty running, climbing steps, or rising from a chair; and a fine tremor of the fingers. The lower extremities are most often affected. Complications include scoliosis and joint contractures—chronic shortening of muscles or tendons around joints, caused by abnormal muscle tone and weakness, which prevents the joints from moving freely.

Symptoms of Fazio-Londe disease appear between 1 and 12 years of age and may include facial weakness, dysphagia (difficulty swallowing), stridor (a high-pitched respiratory sound often associated with acute blockage of the larynx), difficulty speaking (dysarthria), and paralysis of the eye muscles. Most individuals with SMA type III die from breathing complications.

Kennedy disease, also known as progressive spinobulbar muscular atrophy, is an X-linked recessive disease. Daughters of individuals with Kennedy disease are carriers and have a 50 percent chance of having a son affected with the disease. Onset occurs between 15 and 60 years of age. Symptoms include weakness of the facial and tongue muscles, hand tremor, muscle cramps, dysphagia, dysarthria, and excessive development of male breasts and mammary glands. Weakness usually begins in the pelvis before spreading to the limbs. Some individuals develop noninsulin-dependent diabetes mellitus. The course of the disorder varies but is generally slowly progressive. Individuals tend to remain ambulatory until late in the disease. The life expectancy for individuals with Kennedy disease is usually normal.

Congenital SMA with arthrogryposis (persistent contracture of joints with fixed abnormal posture of the limb) is a rare disorder. Manifestations include severe contractures, scoliosis, chest deformity, respiratory problems, unusually small jaws, and drooping of the upper eyelids.

Post-polio syndrome (PPS) is a condition that can strike polio survivors decades after their recovery from poliomyelitis. PPS is believed to occur when injury, illness (such as degenerative joint disease), weight gain, or the aging process damages or kills spinal cord motor neurons that remained functional after the initial polio attack. Many scientists believe PPS is latent weakness among muscles previously affected by poliomyelitis and not a new motor neuron disease.

Symptoms include fatigue, slowly progressive muscle weakness, muscle atrophy, fasciculations, cold intolerance, and muscle and joint pain. These symptoms appear most often among muscle groups affected by the initial disease. Other symptoms include skeletal deformities such as scoliosis and difficulty breathing, swallowing, or sleeping. Symptoms are more frequent among older people and those individuals most severely affected by the earlier disease. Some individuals experience only minor symptoms, while others develop SMA and, rarely, what appears to be, but is not, a form of ALS.

In certain embodiments, the antibodies and compositions provided herein may be used to prevent or treat motor neuron diseases, such as those described herein, and in particular ALS. In an embodiment, the antibodies provided herein are used to prevent or treat ALS in a subject in need thereof. In another embodiment, the antibodies and compositions provided herein are used to prevent or treat a motor neuron disease selected from the group consisting of ALS, progressive bulbar palsy, pseudobulbar palsy, primary lateral sclerosis, progressive muscular atrophy, spinal muscular atrophy, SMA Type I, SMA type II, SMA type III, Fazio-Londe disease, Kennedy disease, congenital SMA with arthrogryposis, and post-polio syndrome.

As used herein the term "subject" may include animals, such as mammals, such as dogs, cats, cows, pigs, sheep and horses, and human. In a particular embodiment, the subject is a human. In yet another embodiment, the subject is an adult human.

EXAMPLES

The present invention will be more readily understood by referring to the following examples, which are provided to illustrate the invention and are not to be construed as limiting the scope thereof in any manner.

Experimental Procedures

Cell Lines

Mouse SP2/0 myelomas; nnr5 cells (derived from rat PC12 pheochromocytoma) and which express p75 but not Trk receptors, nnrr5 cells stably transfected with human TrkC cDNA (nnr5-TrkC), NIH-3T3 transfected with human trkC cDNA (NIH-TrkC cells) or human trkA cDNA (NIH-TrkA cells), and wild type NIH-3T3 cells were used. All cells were cultured in RPMI media supplemented with 5% fetal bovine serum (FBS) and antibiotics (Gibco). Stable transfectants were added the appropriate drug selection, and protein expression was routinely verified.

Co-Expression of Full Length p75 Receptors

NIH-TrkC cells were stably transfected with full length rat p75 receptor with pcDNA3.1/Zeo(+) p75 construct. Stable transfectants were selected by treatment with Zeocin (200 µg/ml).

Antibodies

Rat anti-mouse IgG (αmIgG; Sigma, St. Louis, Mo.), anti-phosphotyrosine mAb 4G10 (Upstate Biotechnology, Lake Placid, N.Y.), anti-phospho-AKT (ser473) antibody (Cell Signaling), anti-phospho-MAPK (p42/44, thr202/tyr204) antibody (Cell Signaling), and fluoresceinated [fluorescin isothiocyanate (FITC)] goat anti-mouse IgG (FITC-GαmIgG) (Sigma, St. Louis, Mo.) and goat anti mouse Fab (GαmFab) antibodies were purchased commercially. MAb 5C3 was developed and grown in our laboratory (LeSauteur et al., 1996, J. Neurosci. 16: 1308-1316) and is an agonistic anti-TrkA mAb directed to the TrkA-D5/juxtamembrane domain. Rabbit antisera 203 that binds to all Trks was a gift of David Kaplan (Univ. of Toronto) and rabbit antisera to TrkC ectodomain protein was a gift of Lino Tessarrollo (National Cancer Institute).

Peptide Immunogen

A peptide (ESTDNFILFDEVSPTPPI)(SEQ ID NO: 1) spanning a sequence near the D5 domain of human TrkC was synthesized and was conjugated to KLH as carrier. The 18 amino acid ectodomain sequence is located at the linker region and ends 10 residues before the predicted transmembrane domain. The sequence matches perfectly and with no gaps most primates (e.g. chimpanzee), and has high homology with mouse and rat sequences (ESTDFFDFESDASPTPPI)(SEQ ID NO: 1). The alignment for human/mouse/rat is ESTD-F--FD---+-SPTPPI.

MAb 2B7 Generation and Purification

All animal protocols were approved by McGill Animal Care Committee. Female Balb/c mice (8 weeks old) were immunized three times. Splenocytes were fused to SP2/0 myelomas, and hybridomas were screened by differential binding in an Enzyme-Linked Immunosorbent Assay (ELISA) using the original peptide immunogen conjugated to BSA. Specific binding data to native cell surface receptors were obtained using a Fluorescent Activated Cell Scanner (FACScan) (Becton Dickinson, San Jose, Calif.) (see below). MAb 2B7 [IgG1(κ)] was identified by IsoStrip (Roche) and subcloned three times. MAb 2B7 was purified onto a Protein G-Sepharose column (Sigma). The binding and biochemical properties of purified mAb 2B7 were characterized by ELISA, FACScan, and SDS-PAGE.

Monomeric mAb 2B7 Fabs

MAb 2B7 was purified (8 mg/ml) as above and digested with 0.02 mg/ml papain (Gibco, Toronto, Ontario, Canada) for 6 hours (LeSauteur et al., 1996, J. Neurosci. 16: 1308-1316). Fabs were re-purified on Protein A-Sepharose and dialyzed against PBS. Products were characterized by SDS-PAGE under non-reducing conditions.

FACScan

Cells ($2.5 \times 10^5$) in 0.1 ml of binding buffer [Hanks' Balanced Salt Solution (HBSS), 0.1% bovine serum albumin (BSA), and 0.1% $NaN_3$] were incubated with the indicated concentration of mAbs or Fabs for 20 min at 4° C., washed in binding buffer to remove excess primary antibody, and immunostained with FITC-GαmIgG secondary antibody for 20 min at 4° C. Cells were acquired and analyzed on a FACScan-BD Sciences using the Cell Quest program. As negative controls no primary (background fluorescence), or irrelevant mouse IgG (Sigma) were used followed by secondary antibody. Specificity was gauged using various cells expressing different receptors.

Western Blot Analysis

Assays were performed as previously described (Maliartchouk and Saragovi, 1997, J. Neurosci. 17: 6031-6037). The activation of each protein (Trk, Akt and MAPK) was studied after treatment of live cells with different concentrations of ligands mAb 2B7, mAb 2B7 Fabs, NT-3 for 12 minutes at 37° C., cells were solubilized and protein concentrations were determined with Bio-Rad Detergent Compatible Protein Assay (Bio-Rad). Western blot analysis was performed with the indicated reagents. Blots were visualized using the enhanced chemiluminiscence system (PerkinElmer Life Sciences). Re-blotting the membranes with anti-serum directed to total Trk (203 serum from Dr. David Kaplan) or anti-actin antibody (Sigma) confirmed equal protein loading. Quantification of Western blots was done by densitometric analysis relative to total protein levels. Quantification data are presented as percent relative to optimal (10 nM NT-3) as 100%.

Statistical analysis were performed by two-tailed t-tests; statistical significance (p≤0.05) is indicated by an asterisk (*).

Binding Inhibition Assays

MAb 2B7 and mAb 5C3 were labeled with biotin (Pierce). Competition of mAb 2B7 binding to NIH-TrkC or NIH-TrkC+p75 cells was tested with NT-3 or NGF as irrelevant control. The binding assays were first optimized to quantify saturation. Cells were first incubated with various concentrations of the test inhibitor (20 minutes at 4° C.) followed by saturating (~67 nM) of mAb 2B7-biotin, mAb 5C3-biotin as irrelevant primary, or negative control mouse IgG for another 20 minutes at 4° C. Then, FITC-goatαmIgG or FITC-avidin was added as secondary reagent. After washing, cells were analyzed by FACScan as previously described. The conditions used (4° C. and Na azide in the buffer) did not allow internalization.

Proliferation/Survival Assays

NIH-TrkC or NIH-TrkC$^+$p75 cells (7,500 cells/well) in serum-free media (PFHM-II; Gibco) supplemented with 0.2% BSA were added to 96-well plates (Falcon, Lincoln Park, N.J.) containing NT-3, mAb 2B7, mAb 2B7 Fabs, negative control mouse IgG, or serum (final 5% FBS, normal culture conditions). Where indicated, mAb 2B7 Fabs were cross-linked with goat anti-mouse Fab (Gαm Fab). Wells containing all culture conditions but no cells were used as blanks. The growth/survival profile of the cells was quantified using the tetrazolium salt reagent 4-[4,5-dimethylthiazol-2-yl]-2,5-diphenyltetrazolium bromide (MTT; Sigma) 48-72 hours after plating. Optical density readings of MTT were done in a Benchmark Plus microplate Spectrophotometer (BioRad) at 595 nm with blanks subtracted. For the cells used in this paper we have validated the MTT method for measuring cell viability. Almost all the cells die by apoptosis within 72 hours. In this assay "partial survival" or "slower death" correlates with TrkC-pTyr activation.

Differentiation Assays in Cell Lines nnr5 cells stably transfected with TrkC cDNA (nnr5-TrkC) were plated on cover-slips with full media in 24-well plates. 24 hours after plating the indicated treatments were added for an additional 48-72 hours of culture. Cellular differentiation was gauged by immunocytochemistry after cover-slips were fixed and stained with MAP-2 antibody (Chemicon) followed by goat anti-rabbit Cy3 (Jackson Immunochemicals) and analyzed as described earlier (Ivanisevic et al, 2003, Oncogene 22: 5677-5685).

Dendritic Development Assays in Hippocampal Neurons

Primary cultures of hippocampal neurons were prepared from rats (E18) as previously described (Kaech and Banker, 2006, Nat. Protoc. 1: 2406-2415). Neurons were plated on poly-L-lysine coated coverslips at low density (~6000 neurons/cm$^2$) in minimum essential medium (MEM) containing 10% horse serum, 0.6% glucose, 2 mM glutamine and antibiotics. After 5-8 hours, medium was replaced for Neurobasal media (GIBCO, Invitrogen, USA) containing 1 mM glutamine, B-27 supplement and antibiotics. These neuronal cultures do not express detectable p75 (data not shown, see (Bronfman et al., 2007, Dev. Neurobiol. 67: 1183-1203)). This is consistent with this stage for neurons in vivo, where p75 is undetectable by immunohistochemistry in the hippocampal formation of the adult rat brain. One day after plating, neurons were treated with saturating concentrations of neurotrophins (NT-3, BDNF, 6.7 nM) or 2B7 (100 nM). After 7 days of treatment, neurons were fixed 15 minutes with 3% paraformaldehyde, 4% sucrose in PBS. For immunostaining, fixed neurons were incubated with glycine 0.15 M, pH 7.4, for 10 minutes and then washed. Neurons are then permeabilized with 0.2% saponin, non-specific binding was blocked with 3% BSA, and immunostaining was done with mAb MAP2 (Chemicon, Millipore), followed by incubation with anti-Mouse Alexa 555 secondary antibody (Molecular Probes).
Image Analysis and Quantification Z-series of individual immunostained neurons was acquired with a Zeiss LSM Pascal 5 (Carl Zeiss, USA) connected to an inverted microscope (Axiovert 2000) with a 63× objective. Z-series of each neuron were integrated in a single image for morphometrical analysis of the complete dendritic arbor. Quantitative analysis of dendritic arborization was performed using ImageJ software (NIH, USA) as previously described by Sholl (Sholl, 1953, J. Anat. 67: 387-406). For each neuron, concentric circles spaced 10 µm apart starting from the center of cell body was traced. The number of dendrites that intersect each circle was counted and plotted as a function of distance from the soma. The total length of neurites and branch length per branch order was analyzed using the "ImageJ" plugin called "NeuronJ". Neurites were traced manually and labeled as primary (originated directly from the soma), secondary (branching from a primary) and tertiary (branching from a secondary). Since the MAP2 antibody labels all neurites, it is not possible to accurately assign axons and dendrite nomenclature. Instead, the program uses an order of primary-secondary-tertiary branches to perform the calculations. Once branch order nomenclatures were assigned, the neurite tracings appeared color-coded by type and a text file containing neurite total length and branch length per branch order measurement data was generated. The average of the total length of neurites and average of branch length per branch order were calculated and t-test was applied for statistical analysis ($p \leq 05$ considered significant).
ALS Therapeutic Paradigms
Transgenic Murine Models of ALS Transgenic mice are available that express mutant human SOD1 protein and develop a motor neuron syndrome clinically and neuropathologically similar to human ALS. B6.Cg-Tg(SOD1*G93A)1Gur/J (JAX Labs, stock #004435) mice over express the human SOD1 gene with the G93A mutation in CBL/black 6 background; these mice have an average 50% survival at 157.1+9.3 days.
Mouse Behavior Mice were weighed and assessed for motor function and behavior at least twice prior to the treatment.
Hindlimb Extension Reflex Reduction in hindlimb extension when animals are lifted by the tail is an early deficit observed in mutant SOD1 transgenic mice. Animals were lifted by the base of the tail and hindlimb extension was scored. Score 4 indicates full extension of both hindlimbs. Score 3 indicates normal extension of one hindlimb, but poor or inconsistent extension of the other. Score 2 indicates normal extension of one hindlimb, and no extension of the other. Score 1 indicates poor or inconsistent extension of one hindlimb, and no extension of the other. Score 0 indicates no hindlimb movement. This test was done weekly until death or euthanasia.
Rotarod Mice were placed on a 1¼ inch diameter drum that is rotated at a pre-determined speed, and the time taken until they drop was automatically recorded by a sensor in the landing platform. This test was performed weekly.
Endpoints and Analysis Once the mice have a hindlimb reflex score of less than 2 they are considered to be in late stage disease and are monitored and weighed on a daily basis. At this stage of disease progression, mice were tested daily for a righting reflex. The animal is placed on its back or side and the time it takes for the animal to stand up on its paws is measured. The animal is considered to have reached its study endpoints if it cannot right itself within 30 seconds of being placed on its side or back or if it loses more than 20% of its body weight. If either of these endpoints is reached, the animal must be euthanized. Survival is scored until death ensues or euthanasia is mandated.

Example 1

Generation and Initial Screening of mAb 2B7 Binding

Linear peptide $NH_2$-ESTDNFILFDEVSPTPPI-COOH (SEQ ID NO: 1) was conjugated through the N-terminus to KLH, and was used to immunize mice. After fusion of splenocytes with SP2 myeloma cells, culture supernatant from hybridomas was screened by ELISA using either the immunizing peptide conjugated to BSA, or free peptide immobilized on the ELISA plate. Several independent wells with hybridoma cells producing antibodies with selectivity to the immunizing peptide were identified, and they were subcloned three times by limiting dilution. MAb 2B7 was chosen for further work.

Example 2

Characterization of mAb 2B7 Binding

To assess mAb 2B7 specificity for cell surface TrkC, cells expressing or lacking TrkC were screened for differential binding by FACScan.

MAb 2B7 binds strongly to NIH-TrkC transfectants (FIG. 1C) and nnr5-TrkC transfectants (FIG. 1F). In controls, it does not bind to wild type NIH-3T3 cells (FIG. 1A), NIH-TrkA transfectants (FIG. 1B), or wild type nnr5 cells (FIG. 1E) above mIgG background control. In additional assays mAb 2B7 does not bind to SY5Y cells transfected with human TrkB cDNA (data not shown). Binding of mAb 2B7 to non-permeabilized cells indicates that it recognizes the extracellular domain of TrkC. The specific epitope on TrkC is located between the transmembrane and the D5 domain. Therefore, mAb 2B7 binds selectively to native TrkC on the cell surface; near the juxtamembrane region; and it does not bind to p75, TrkB, or TrkA.

The concentration of mAb 2B7 and mAb 2B7 Fab required for saturation of TrkC (FIG. 1I) is ~65 nM mAb 2B7 and ~75 nM 2B7 Fab. The slight difference in fluorescent intensity at saturation with intact mAb versus Fabs is due to the use of different fluorescinated secondary reagents.

Western blot analysis with mAb 2B7 reveals a band at $M_r$ 145 kDa (p145) for lysates from NIH-TrkC, but no bands for lysates of control wild type NIH-3T3 cells (FIG. 1J), or for NIH-TrkA cells (data not shown). MAb 2B7 is effective in western blot analysis only when samples were prepared under non-reducing conditions, which suggests the influence of a disulfide bond.

Example 3

Ligand Competition Studies

FACScan analysis demonstrated that NT-3 blocks, in a dose-dependent manner, mAb 2B7 binding sites. NT-3 at 1 nM blocks ~40% of the mAb 2B7 binding sites in NIH-TrkC (FIG. 1G) and in NIH-TrkC+p75 cells (FIG. 1H; see Table 1 for a summary). Thus, mAb 2B7 binds to a receptor hot spot topologically related to the NT-3 binding site, but which is outside the known NT-3 binding site demonstrated to be exclusively at the D5 domain of TrkC. The block of NT-3 upon 2B7 binding could be due to steric inhibition or allosteric inhibition. These results suggest that assays to screen for agents that inhibit mAb 2B7 binding to TrkC can be used to identify TrkC ligands.

Table 1 shows a summary of FACScan data from FIGS. 1G and 1H. Raw mean channel fluorescence (MCF) for a single experiment is shown, and mAb 2B7 inhibition of binding by NT-3 are presented as % inhibition±sem, n=3 independent experiments. Mouse IgG is used as background control (no binding). MAb 2B7 is used at saturating concentrations.

TABLE 1

NT-3 competes 2B7 binding

| Fluorescent Antibody | Added NT-3 Competitor | Mean Channel Fluorescence | | % inhibition of 2B7 binding | |
|---|---|---|---|---|---|
| | | TrkC cells | TrkC + p75 cells | TrkC cells | TrkC + p75 cells |
| 2B7 | 0 nM | 95 | 56 | | |
| 2B7 | 0.1 nM | 87 | 42 | 14 ± 4 | 30 ± 2 |
| 2B7 | 1.0 nM | 63 | 33 | 43 ± 8 | 49 ± 5 |
| mIgG control | — | 11 | 10 | | |

Example 4

Co-Expression of p75NTR Reduces the 2B7 mAb Binding Sites on TrkC, an Effect that Requires the Extracellular Domain of p75NTR Co-expression of full length $p75^{NTR}$ in NIH-TrkC cells reduces the cell surface 2B7 binding sites by ~50-60% in quantitative FACScan assays. This reduction was observed in all twelve NIH-TrkC⁺p75 clones that were independently isolated (FIG. 1D, also see Table 1). Higher concentrations of mAb 2B7 do not overcome the reduction in binding sites elicited by expression of p75.

Quantitative Western blot analyses of three NIH-TrkC⁺p75 clones, using mAb 2B7, demonstrated levels of total TrkC comparable to those in parental NIH-TrkC cells (FIG. 1K), and similar data were obtained using anti-TrkC rabbit serum (data not shown). These data indicate that expression of p75 does not reduce expression of TrkC. Rather, expression of p75 may induce conformational changes or steric hindrance at or near the mAb 2B7 epitope on TrkC. This would be suggestive of physical or allosteric p75•TrkC interactions that prevent mAb from binding to TrkC. This suggestion is further supported by the observed inverse correlation between p75 levels and the level of blocking of mAb 2B7 binding to TrkC. In different clones, low expression of p75 reduces 2B7 binding weakly, while high expression of p75 reduces 2B7 binding strongly (data not shown).

To determine which domain of p75 was relevant to block the 2B7 mAb binding sites on TrkC, we transfected a p75 construct expressing the transmembrane domain (TM) and intracellular domain (ICD) but which had the ectodomain (ECD) deleted. High expression of the deletion p75 mutant was verified through an engineered tag. The expressed p75-TM-ICD is not sufficient to block mAb 2B7 binding to TrkC (data not shown). Thus, we conclude that the p75 ECD is required for blocking mAb 2B7 binding to TrkC.

Example 5 p75NTR Blocking of 2B7 mAb is not Regulated by p75 Ligands

Because the p75 blocking of 2B7 mAb binding requires the p75-ECD, we tested whether selective ligands of p75 could release the hindrance to 2B7•TrkC interactions. In NIH-TrkC⁺p75 cells, NGF, BDNF, and pro-NT-3 (Alomone Labs) were added first to engage p75, because in this paradigm they act as p75-selective ligands. Then, cells were analyzed in quantitative FACScan assays with mAb 2B7. None of the p75 ligands afford an increase or a decrease in 2B7 binding (data not shown). The data suggest that whether or not it is liganded, p75 can reduce 2B7•TrkC binding.

As an interesting side point, pro-NT-3 does not reduce the mAb 2B7 binding sites on NIH-TrkC cells either (data not shown), whereas mature NT-3 does (FIG. 1G). These data indicate that pro-NT-3 does not bind to this particular region of TrkC receptors.

Example 6

Agonism by mAb 2B7 and Monomeric mAb 2B7 Fabs

Biochemical assays (FIG. 2), survival assays (FIG. 3), and differentiation assays (FIG. 4) were undertaken to determine if mAb 2B7 has NT-3-like agonistic activity.

Figure 2:
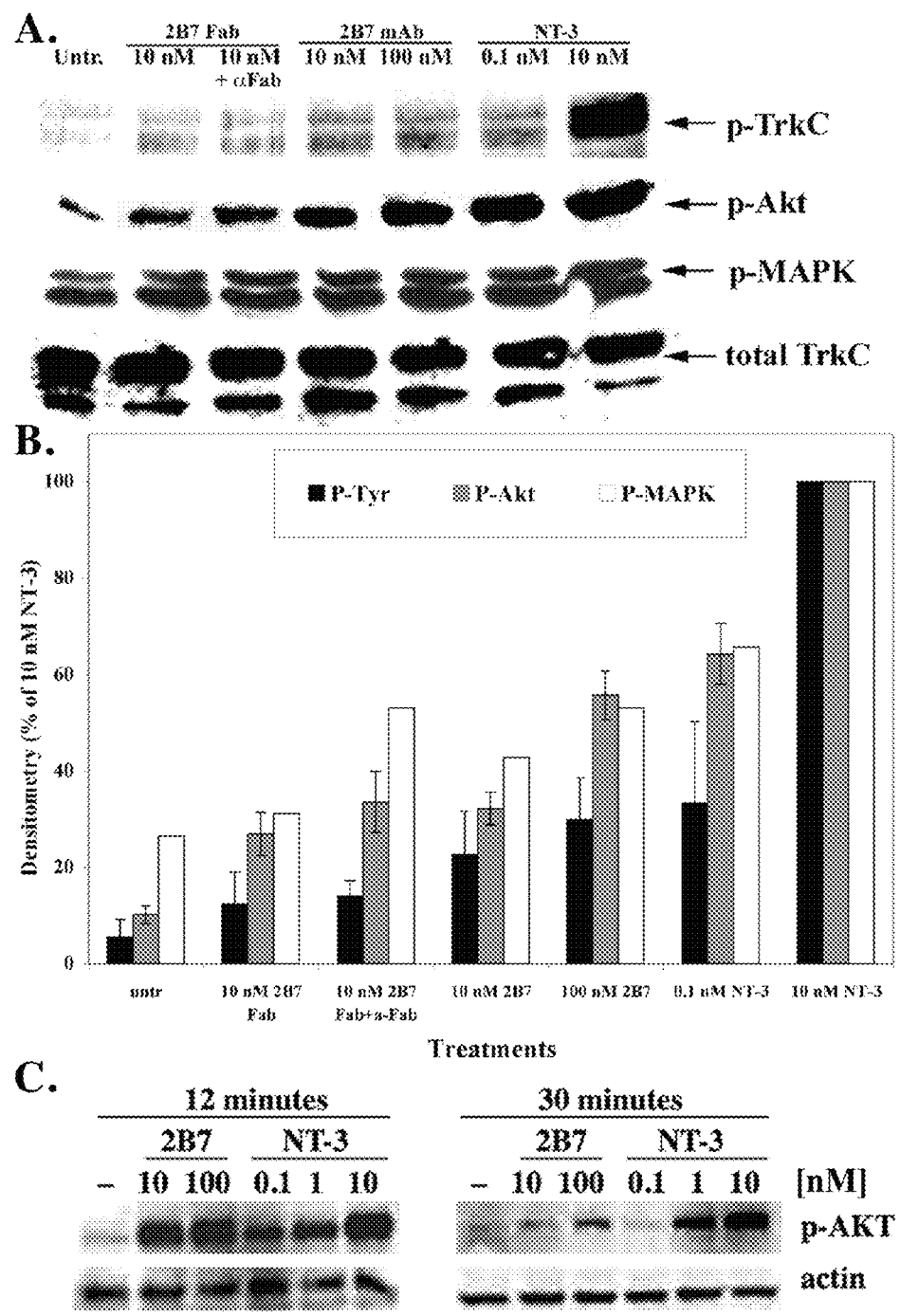
FIG. 2 shows that TrkC, Akt and MAPK activation are induced by mAb 2B7 or mAb 2B7 Fabs. NIH TrkC cells were treated with the indicated ligands for 12 minutes and cell lysates were analyzed by Western blot. (A) shows anti-P-Tyr, anti-P-Akt, anti-P-MAPK, and total Trk (anti-sera 203, from Dr. David Kaplan). A representative experiment is shown. (B) shows a summary of data quantification by densitometry standardized to total Trk and presented as % relative to 10 nM NT-3 (Anti-P-Tyr, n=3; anti-p-Akt, n=3; anti-p-MAPK n=2). (C) shows anti-p-Akt blots as in (A), wherein NIH TrkC cells were treated with the indicated ligands for 12 or 30 minutes.

Phosphorylation of TrkC, AKT and MAPK were studied in lysates from cells that had been exposed for 12 minutes to ligands or controls (FIG. 2). NT-3, mAb 2B7 and 2B7 Fabs (with or without cross-linking using GαmFab antibodies) afford significant tyrosine phosphorylation of TrkC (p-TrkC) over basal levels in untreated cells (FIG. 2A).

NT-3, mAb 2B7 and 2B7 Fabs also activate downstream signaling proteins MAPK (~2-fold over baseline) and AKT (~5-fold over baseline) (FIG. 2A). The quantification of phosphorylated proteins after 12 minutes of activation, relative to total Trk protein loaded, are presented as % of optimal NT-3 (10 nM, 100% efficacy) (FIG. 2B). p-TrkC is induced by 0.1 nM NT-3 or by 10 nM 2B7 with ~30% efficacy, and by 2B7 Fabs (or 2B7 Fabs cross-linked with GαmFabs) with ~15% efficacy. p-Akt and p-MAPK are induced by 0.1 nM NT-3 and 10 nM 2B7 with ~60% efficacy, and by 2B7 Fabs (or 2B7 Fabs cross-linked with GαmFabs) with ~30% efficacy. In cellular controls studying NIH-TrkA cells, there is no increase in p-TrkA, p-AKT, or p-MAPK after treatment with 2B7 mAb, or 2B7 Fabs (data not shown).

A longer time-course study of p-AKT (12 minutes, and 30 minutes of ligand treatment) showed that activation by NT-3 was sustained, while activation by 2B7 was less efficient long term. At the 30 min point p-AKT by NT-3 remains high ~70% relative to that seen at 12 min, whereas p-AKT by 2B7 is significantly reduced and is <20% relative to that seen at 12 min (FIG. 2C). Therefore, activation by mAb 2B7 is transient compared to that of NT-3.

Figure 3:
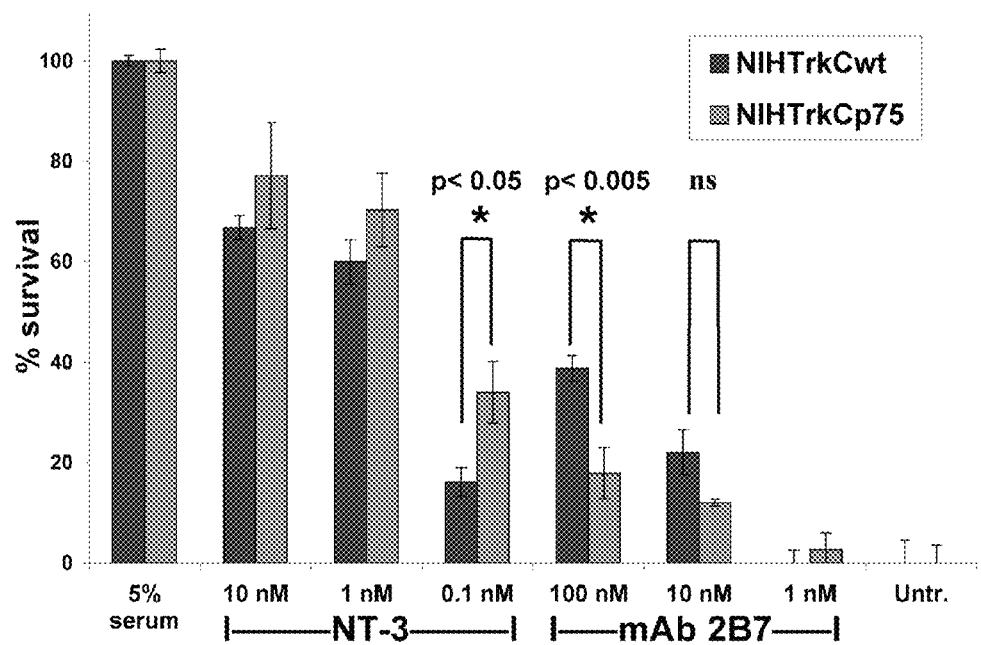
FIG. 3 shows that co-expression of p75 with TrkC hinders the trophic protection of mAb2B7. The survival of NIH-TrkC or NIH-TrkC$^+$p75 cells was tested in MTT assays after culture in SFM supplemented with the indicated ligands or controls (5% serum=100%, untreated=0%, n=4 for each assay). Data are representative from 3 independent experiments. * indicates statistical significance, and ns indicates not statistically significant.
Figure 4:
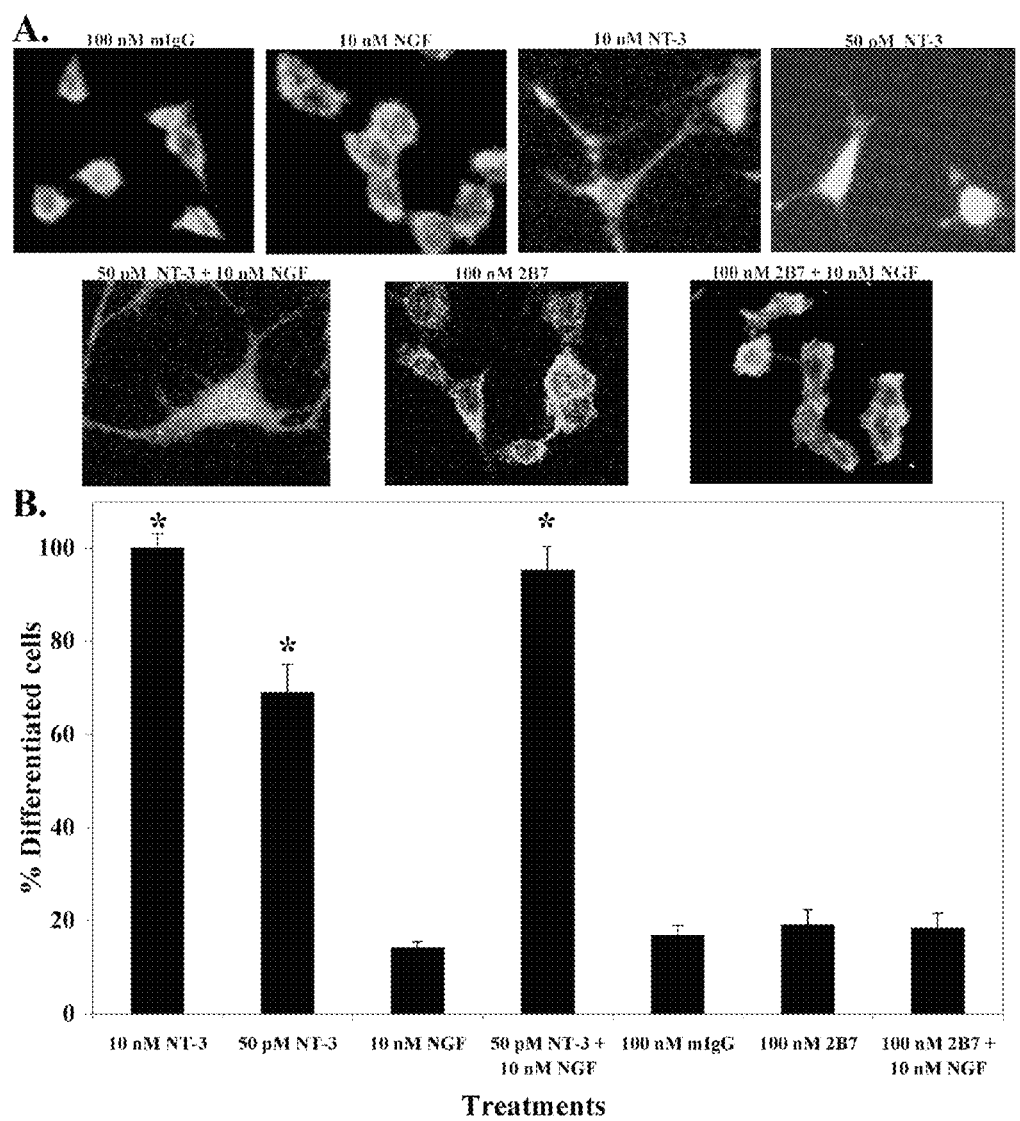
FIG. 4 shows that mAb 2B7 does not induce differentiation of nnr5 TrkC cells. (A) shows representative pictures of the differentiation of nnr5-TrkC cells in response to treatment with the indicated ligand for 48-72 hours. After treatment with the ligand, cells were fixed and immunostained with MAP-2 antibody (Chemicon) followed by goat anti-rabbit Cy3 (Jackson Immunochemicals) and analyzed as described (Ivanisevic et al., 2003, Oncogene 22 5677-5685). (B) shows a quantitative summary (±SD) of 3 independent experiments. Cells were plated with the indicated treatments or controls, and differentiation was scored as % of cells with neurites (>2 cell body long). * indicates statistical significance relative to 100 nM mIgG, $p \le 0.05$. The figure shows that 50 pM NT-3 affords significantly lower cellular differentiation than 10 nM NT-3, while a combination of 50 pM NT-3+10 nM NGF (as a p75 ligand) affords significantly higher cellular differentiation than each ligand alone, and achieves levels comparable to 10 nM NT-3.

These ligands were then tested for their ability to protect cells from death induced by culture in serum-free media (SFM) (FIG. 3). This cellular death is known to be apoptotic. In MTT assays NT-3, mAb 2B7, and monovalent 2B7 Fabs significantly delay the death of NIH-TrkC cells in a dose-dependent manner. Compared versus optimal NT-3, mAb 2B7 has a maximal efficacy of ~45%. Monomeric 2B7 Fabs have a maximal efficacy of ~35% (data not shown). These data correlate with induction of pAKT, which is known to be involved in mediation of trophic support.

Similar MTT assays compared the effects of TrkC agonists on NIH-TrkC cells versus NIH-TrkC$^+$p75 cells (FIG. 3). The purpose was to test the effect of p75 expression on 2B7 agonistic activity. Because these two cell lines have different survival profiles in response to NT-3, the data here is standardized to normal serum growth conditions (100%). The death of NIH-TrkC and NIH-TrkC$^+$p75 cells are both reduced by 10 nM NT-3 to a comparable degree, ~65-70%. As expected, expression of full-length rat p75 in NIH-TrkC cells significantly enhances the efficacy of 0.1 nM NT-3 (35% survival in NIH-TrkC$^+$p75 versus 20% in NIH-TrkC). In contrast, p75 expression significantly reduces the efficacy of mAb 2B7 (20% survival in NIH-TrkC$^+$p75 cells versus 45% in NIH-TrkC).

Thus, expression of p75 improves the binding and the function of NT-3 but reduces the binding and the function of mAb 2B7. These data correlate with a reduction of mAb 2B7 binding when p75 is co-expressed.

Example 7

Effect of p75 Ligands on 2B7 Agonistic Activity

We have previously shown that p75 negatively regulates the efficacy of selective TrkA agonists such as mAb 5C3 (LeSauteur et al., 1996, J. Neurosci. 16: 1308-1316). In this scenario, p75 ligands such as anti-p75 mAb MC192 neutralize the negative regulation of p75 and thus allow full TrkA activation (Maliartchouk and Saragovi, 1997, J. Neurosci. 17: 6031-6037). We therefore performed survival assays with mAb 2B7±engagement of p75 with NGF, BDNF, or anti-p75 mAb MC192.

The ligands are p75-selective in NIH-TrkC$^+$p75 cells, and do not enhance or reduce the survival-promoting signals of mAb 2B7 (data not shown). Thus, the negative regulation of p75 upon mAb 2B7 survival function is not affected by p75-ligands. These data are consistent with our earlier data showing that p75-ligands do not reverse the block to mAb 2B7 binding; and with a report that p75•TrkC functional interactions differ from p75•TrkA functional interactions (Ivanisevic et al., 2003, Oncogene 22 5677-5685).

Example 8

Effect of mAb 2B7 on the Differentiation of Cell Lines

We next tested neurite outgrowth in response to mAb 2B7 (FIG. 4A, data summarized in FIG. 4B). Treatment with mAb 2B7 does not induce the differentiation of nnr5-TrkC cells. This was puzzling because mAb 2B7 binds to the cell surface of nnr5-TrkC cells (FIG. 1F). In positive control assays, nnr5-TrkC cells differentiate in response to NT-3, in a dose-dependent manner. NT-3 increases the percent of cells bearing>2 axons with axonal length>2 cell bodies. In negative control assays, treatment with mIgG or 10 nM NGF do not differentiate nnr5-TrkC cells.

Because p75 can regulate TrkC-mediated signals, including cellular differentiation (Ivanisevic et al., 2003, Oncogene 22 5677-5685), we tested whether mAb 2B7 in combination with selective p75 ligands may afford cellular differentiation. mAb 2B7 combined with the p75-selective ligands NGF (FIG. 4) or BDNF (data not shown) do not stimulate differentiation. In contrast, in positive controls, a suboptimal concentration of 50 pM NT-3 in combination with NGF as a p75-selective ligand increases cellular differentiation. This control combination achieves levels comparable to optimal 10 nM NT-3, as reported previously (Ivanisevic et al., 2003, Oncogene 22 5677-5685).

Thus, mAb 2B7 activates TrkC but it does not have intrinsic neuritogenic activity in the nnr5-TrkC cell line, and the use of p75 ligands does not potentiate neurogenesis either.

Example 9

Effect of BDNF, NT-3, and mAb 2B7 on Dendritic Arborization in Primary Neuronal Cultures Primary cultures of E18 rat hippocampal neurons were prepared (Kaech and Banker, 2006, Nat. Protocol 1: 2406-2415) and plated at low density (~6000 neurons/cm$^2$) as described in Neurobasal/B27. Under these conditions expression of p75 is barely detectable by western blotting and is undetectable by immunohistochemistry (Bronfman et al., 2007, Dev. Neurobiol. 67: 1183-1203). This is consistent with this stage of development for neurons in vivo, where p75 is undetectable by immunohistochemistry in the hippocampal formation of the adult rat brain. Neuronal cultures were treated with saturating concentrations of NT-3, BDNF (6.7 nM) or 2B7 (100 nM), and the morphology of the dendritic arbor was analyzed after 7 days treatment as described in the Methods.

Figure 5:
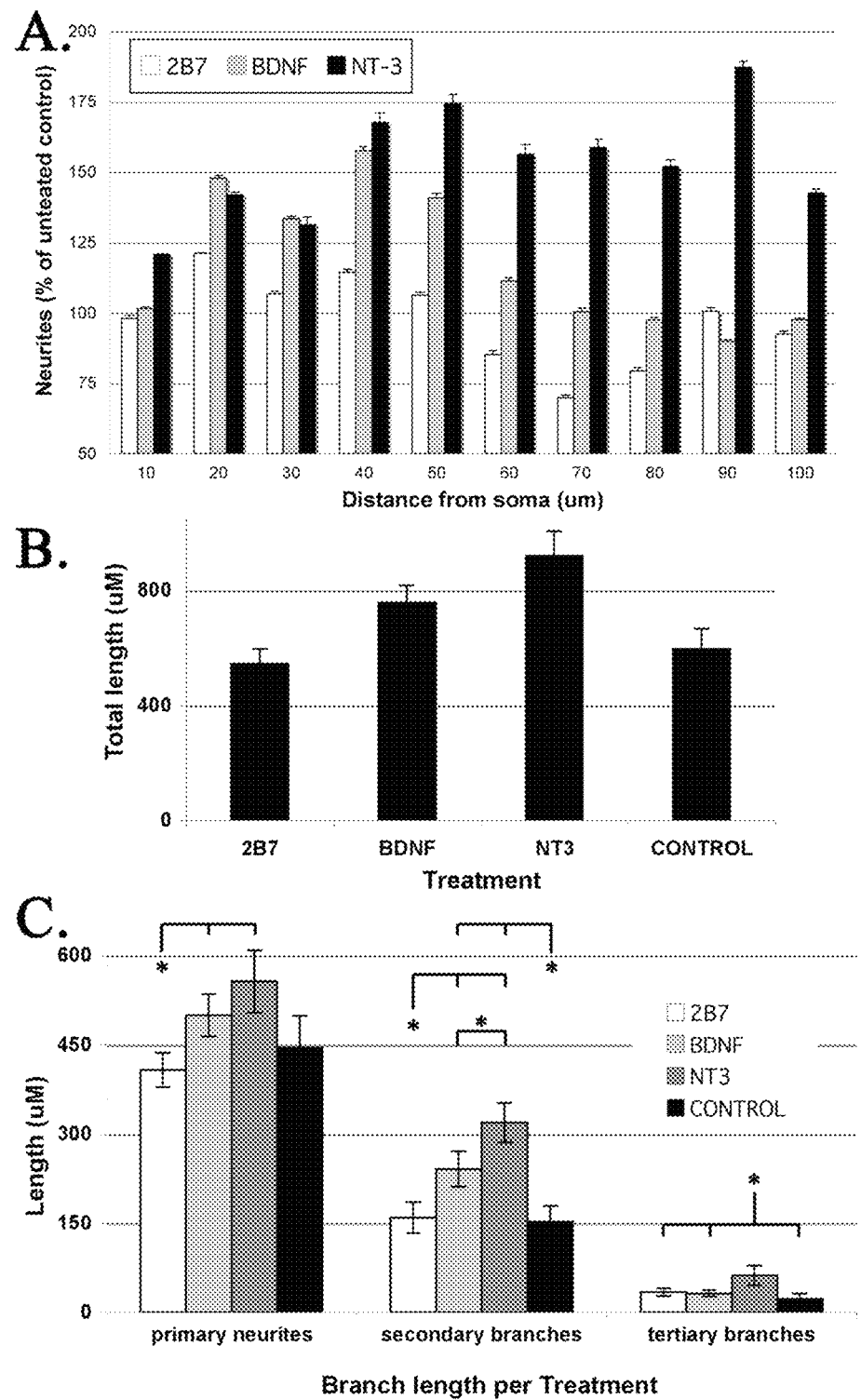
FIG. 5 shows that mAb 2B7 does not induce differentiation of primary neuronal cultures. Hippocampal neurons were plated with indicated treatments, and differentiation was scored as % of control cells. (A) shows a Sholl analysis of dendritic intersections as a % of untreated control cells. NT-3 and BDNF have a significant effect on the morphology of the dendritic arbor, with a higher number of primary dendrites and branching. NT-3 has longer dendrites compared to BDNF, whereas mAb 2B7 did not have any effect on the development of the dendritic arborization. In (B) the average of the total length of neurites and average of branch length per branch order was further assessed using NeuronJ. BDNF and NT-3 significantly increased the total length of neurites compared to control-untreated cells, but NT-3 treatment was more effective. The mAb 2B7 did not have any effect on the growth of neurites compared to control. All comparisons are statistically significant ($p<0.05$) except control versus 2B7 treatment. (C) shows analysis of the branch length per branch order. MAb 2B7 did not cause any change in the elongation of neurites. NT-3 increases the length of both secondary ($p<0.001$) and tertiary order branches ($p<0.05$), whereas BDNF increases the length of secondary order branches ($p<0.01$). Asterisk indicates $p<0.05$.

The data of the morphology of the dendritic arbor are illustrated in FIG. 5. The histogram on FIG. 5A represents the Sholl analysis of dendritic intersections as % of untreated control cells. Both NT-3 and BDNF have a significant but differential effect on the morphology of the dendritic arbor. Both NT-3 and BDNF treatment result in a higher number of primary dendrites (projections from the cell body of the neuron) and an increase in dendritic branching. However, NT-3 resulted in longer dendrites compared to BDNF. Compared to NT-3 or BDNF the mAb 2B7 did not have any effect on the development of the dendritic arborization of hippocampal neurons, suggesting that the mAb is not able to trigger morphological differentiation as NT-3.

The average of the total length of neurites and average of branch length per branch order was further assessed using NeuronJ (FIG. 5B). Both BDNF and NT-3 significantly increased the total length of neurites compared to control-untreated cells ($p<0.05$, $p<0.01$, respectively). Interestingly, NT-3 treatment resulted in longer neurites compared to BDNF ($p<0.05$). The mAb 2B7 did not have any effect on the growth of neurites compared to control.

A further detailed analysis of the branch length per branch order (FIG. 5C) reveals that, compared to control, BDNF increases the length of secondary order neurites ($p<0.01$) whereas NT-3 increases the length of both, secondary ($p<0.001$) and tertiary order neurites ($p<0.05$). NT-3 had a bigger effect on the length of secondary and tertiary branches compared to BDNF ($p<0.05$), indicating that NT-3 results in longer neurites, as we have indicated by Sholl analysis.

Figure 6:
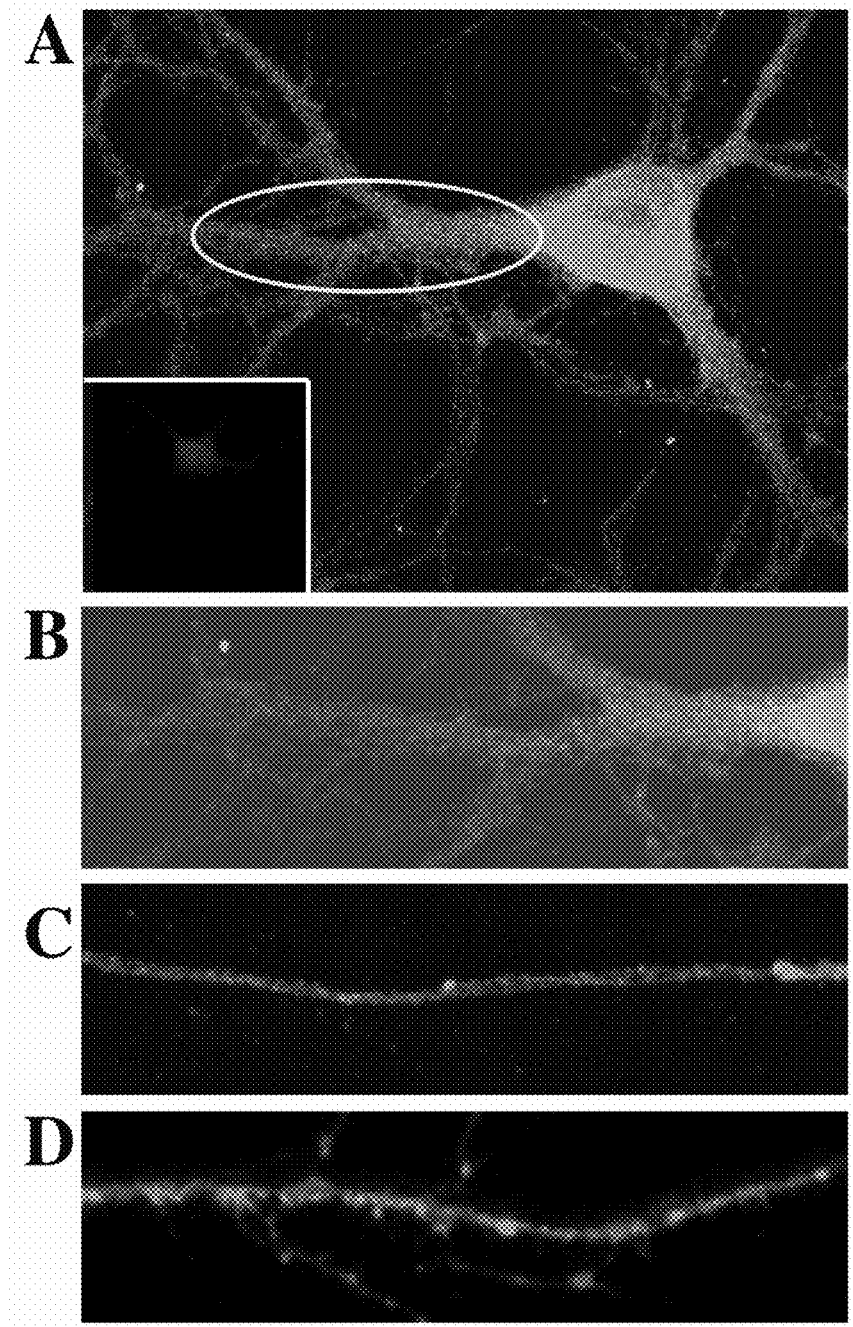
FIG. 6 shows MAb 2B7 immunostaining of primary neuronal cultures. Representative pictures of E18 primary hipoccampal neurons immunostained with mAb 2B7 are shown, wherein A, B, C show confocal images and D shows epifluoresence. Control immunostaining with no 2B7 primary antibody results in no detectable fluorescent signal (inset square, panel A). The image in panel B is a magnification of the area in yellow ellipse from panel A.

Representative confocal immunofluorescence and epifluorescent pictures of neuronal cultures immunostained with mAb 2B7 are shown (FIG. 6). The neuronal cultures look healthy, even if they are not supplemented with growth factor or antibody. Low magnification shows widespread and intense immunostaining of soma and dendrites (FIGS. 6A and 6B). High magnification shows punctate immunostaining in the axons, that appear to be vesicular (FIGS. 6C and 6D).

Thus, the mAb 2B7 did not induce any change in the elongation of neurites in hippocampal neurons. These data are consistent with the results using cell lines, and suggest that 2B7 can support cell survival but does not have any effect on the differentiation process.

Example 10

Effect of mAb 2B7 and 2B7 Monovalent Fabs In Vivo, in a Mouse Model of ALS (G93A SOD1 Mutant Transgenic c57Black/6 Mouse)

Transgenic mice that express mutant human SOD1 protein and develop a motor neuron syndrome clinically and neuropathologically similar to human ALS have an average 50% survival at 157.1+9.3 days. These mice were treated with mAb 2B7 IgG, with 2B7 monovalent Fabs, or with saline vehicle. Treatment was initiated when the cohort exhibited signs of disease, based on poor hindlimb extension reflex tests (approximately at age 100 days). Treatment was done by intraperitoneal injections of 0.5 mg/kg of test reagent, in 100 microliters of saline, three times a week, for 10-12 weeks.

Figure 7:
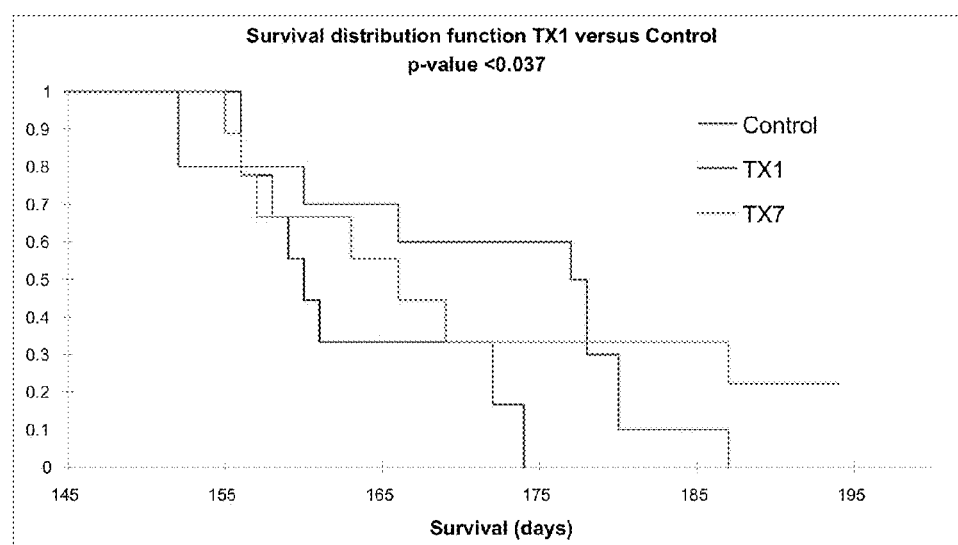
FIG. 7 shows survival distribution function in G93A mutant SOD1 transgenic mice. Survival plot showing % of mice surviving at the indicated age (days). The indicated treatment was started at age ~day 98 (when early symptoms are evident, e.g. poor hind leg reflex in the cohort). Route: intraperitoneal injections, three times a week, 0.5 mg/kg each dose (~10 micrograms per mouse per injection). Duration of treatment 12 weeks. Control=saline vehicle. TX1=treatment with 2B7 Fab monovalent. TX7=treatment with 2B7 IgG.
Figure 8:
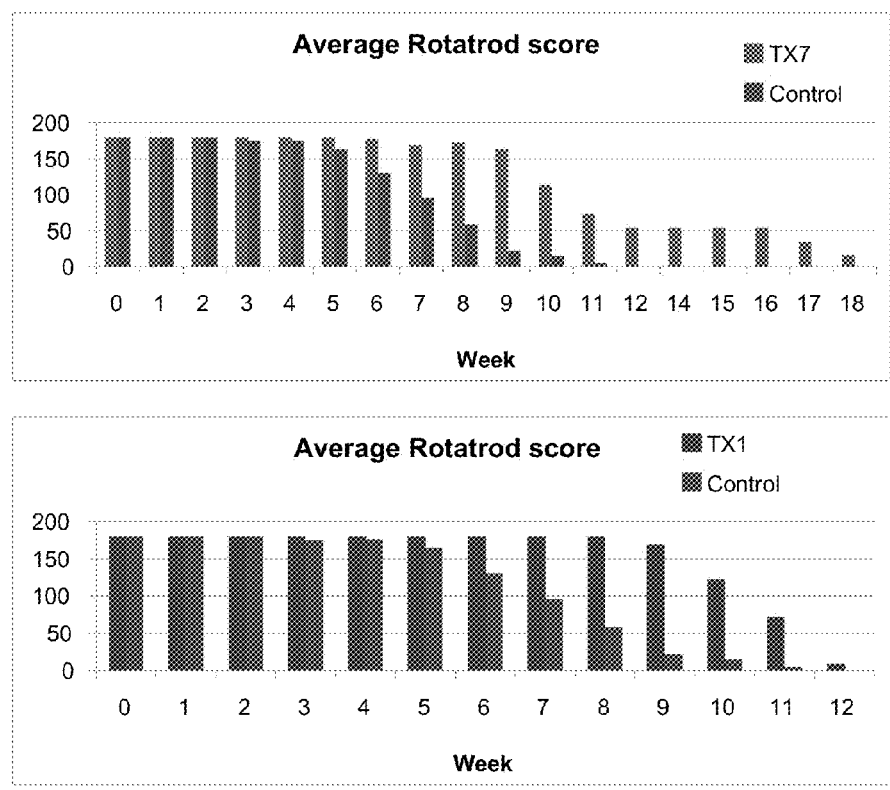
FIG. 8 shows average rotarod scores, indicative of motor function, in G93A mutant SOD1 transgenic mice. Average rotarod performance (in seconds) at the indicated age (weeks). Control=saline vehicle. TX1=treatment with 2B7 Fab monovalent. TX7=treatment with 2B7 IgG.

FIG. 7 shows that G93A mutant SOD1 transgenic mice survive longer when treated with a TrkC agonist mAb 2B7 or with 2B7 Fabs. FIG. 8 shows that the motor performance of the same mice in rotarod tests, indicative of motor function, is improved when treated with a TrkC agonist mAb 2B7 or 2B7 Fabs.

The above Examples show that the mAb 2B7 reported herein specifically binds to the TrkC ectodomain, at the juxtamembrane linker region. The results indicate that the mAb 2B7 reported herein is useful for FACScan, immunofluorescence analysis, immunoprecipitation, Western blot analysis, and immunocytochemistry of TrkC.

The epitope of mAb 2B7 defines a previously unknown "hot spot" of TrkC, between the second immunoglobulin domain (D5) and the transmembrane domain. Competition studies between NT-3 and mAb 2B7, shown herein, indicate topological closeness at their binding sites such that at least steric inhibition or allosteric inhbition can occur. Moreover, because mAb 2B7 in western blots can bind to TrkC only under non-reducing conditions, the results suggest that mAb 2B7 recognizes a TrkC conformation stabilized or influenced by a disulfide bond. This suggests a conformationally sensitive docking site because the epitope contains no cysteines and there are no reported disulfide bonds in this region of TrkC.

Biological studies uncovered a unique signal transduction mechanism. MAb 2B7 and its monovalent Fabs mimic NT-3 binding and function. Functional mimicry by mAb 2B7 is indicated by phosphorylation and activation of TrkC, and its downstream signaling partners, and promotion of trophic cell survival. By these criteria, mAb 2B7 is a TrkC partial agonist.

The partial agonistic signals induced by mAb 2B7 include MAPK activation (~2-fold over baseline) and AKT activation (~5-fold over baseline), and both of these levels of activation are comparable to that resulting form treatment with 100 pM NT-3.

However, there are important biological differences between 2B7 and NT-3. First, mAb 2B7 only affords trophic survival but does not induce neuritogenic differentiation in cell lines or in primary neuronal cultures expressing TrkC, and therefore it can be defined as a biased partial agonist. Second, mAb 2B7 does not bind to p75 and is therefore a more selective ligand than NT-3. Third, 2B7 is less potent than NT-3.

The results also suggest that 2B7 Fabs may cause conformational changes in TrkC that induce or stabilize receptor-receptor interactions.

The above examples also show that expression of p75 leads to a reduction of mAb 2B7 binding sites, without a concomitant reduction in TrkC expression, suggesting that that the mAb 2B7 hot spot is either involved in or close to sites of interactions for TrkC•p75.

The above examples further demonstrate that for blocking mAb 2B7 binding to TrkC, the p75-TM-ICD are not sufficient, and the p75-ECD is required. Because the p75-ECD is the domain where ligands can bind p75, we predicted that p75 ligands might alter the "p75-mediated block" of mAb 2B7•TrkC interactions. However, the "p75-mediated block" of mAb 2B7•TrkC interactions appears to be independent of p75 ligands (e.g. they are not required) and furthermore the block is insensitive to the presence of p75 ligands (in this report we used NGF, BDNF, or pro-NT-3, which did not alter the block).

Using mAb 2B7 as a selective TrkC agonist, we show herein that expression of p75 causes a reduction of 2B7•TrkC signals both in terms of potency (e.g. potency requires higher ligand concentrations) and in terms of efficacy (e.g. the overall strength of the response is lower). This is a striking contrast to NT-3, because expression of p75 can enhance the potency of NT-3•TrkC signals without affecting the overall efficacy.

Lower mAb 2B7 potency obviously stems from the fact that p75 causes a reduction in mAb 2B7 binding sites; meaning that fewer TrkC receptors are activated. However, lower efficacy of mAb 2B7 can only be the consequence of the suppression of TrkC signals by p75.

This interpretation would be consistent with a reported reciprocal interplay between TrkA and p75 receptors that regulates signal cascades and ligand binding. Notably, however, there is an important difference between TrkA-p75 and TrkC-p75. Suppression of TrkA signals by p75 is responsive to p75 ligands. In contrast, suppression of TrkC signals by p75 is not responsive to p75 ligands (Ivanisevic et al., 2003, Oncogene 22 5677-5685).

The examples presented herein also show that mAb 2B7 can afford trophic survival but completely lacks neuritogenic differentiation. This result indicates that it is possible to uncouple these signals at the level of the ligand acting through a wild type receptor. It is quite unusual for an agonistic ligand binding at the ectodomain to uncouple signals that are mediated by intracellular adaptor proteins. In this case we detected efficient pAKT but poor pMAPK signals. This would require a limited conformational change in the receptor activation state such that only some (but not all) adaptor proteins can be activated. mAb 2B7 may be a biased agonist because the ankyrin-rich membrane spanning)/Kidins220 protein (ARMS) protein interacts with Trks through their transmembrane domains, leading to prolonged MAPK signaling and differentiation; TrkC receptors within a putative TrkC-ARMS-p75 complex may not be recognized by mAb 2B7, causing the consequent poor MAPK activation. Alternatively, distinct kinetics of ligand-induced receptor internalization can affect the functional outcome towards neuritogenic differentiation or trophic survival, and mAb 2B7 appears to have slower activation kinetics than NT-3.

We have shown herein that MAb 2B7 fulfills the criteria of a receptor ligand: selective binding, high affinity, and saturability. Functional assays demonstrate biased agonistic activity. Biased agonists are of great biological interest, and very few have been documented for receptor tyrosine kinases. In particular, it is intriguing that mAb 2B7 is a biased agonistic ligand because it binds to a "hot spot" partially overlapping with NT-3. These data suggest that engaging a TrkC receptor "hot spot" in the juxtamembrane-linker domain can induce survival signals only. Moreover, this "hot spot" can potentially be regulated by expression of p75, either through direct steric hindrance, or through direct or indirect changes to the TrkC conformation.

Aberrant expression of trkC mRNA have been correlated with neurodegenerative diseases such as Alzheimer's disease (AD), motor neuron diseases such as amyotropic lateral sclerosis (ALS) and some types of cancers, as well as with photoreceptor disorders and glaucoma. Thus, mAb 2B7 or its derivatives are of particular interest for diagnostic, therapeutic, or prophylactic use for these diseases. Also, mAb 2B7 may be useful in disorders where TrkC-mediated trophic support is desired without inducing neuritic growth, differentiation, or new connections.

The contents of all documents and references cited herein are hereby incorporated by reference in their entirety.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

5. The monoclonal antibody or the fragment, portion, variant or derivative of claim 1, wherein the antibody or the fragment, portion, variant or derivative thereof binds and/or activates murine or rat TrkC and/or wherein the antibody or the fragment, portion, variant or derivative thereof does not bind and/or activate TrkA, TrkB and/or p75NTR and/or wherein the antibody or the fragment, portion, variant or derivative thereof binds and/or activates TrkC differently from NT-3 and/or wherein the antibody or the fragment, portion, variant or derivative thereof specifically binds an epitope of human TrkC with a sequence comprising the juxtamembrane region or a portion thereof of human TrkC.

6. A pharmaceutical composition comprising the monoclonal antibody or the fragment, portion, variant or derivative of claim 1 and a pharmaceutically acceptable carrier.

7. A method of activating TrkC in a subject, comprising administering a therapeutically effective amount of the monoclonal antibody or the fragment, portion, variant or derivative of claim 1 to the subject, such that TrkC is activated in the subject.

8. The method of claim 7, wherein the subject is a human and the TrkC is human TrkC.

9. The method of claim 8, wherein the monoclonal antibody or the fragment, portion, variant or derivative is administered in combination with a second therapeutic agent.

10. The method of claim 9, wherein the second therapeutic agent is selected from a muscle relaxant, a tranquilizer, an anticonvulsant, a nonsteroidal anti-inflammatory agent, a benzodiazepine, riluzole and amitriptyline.

11. The method of claim 7, wherein the subject suffers from: a neurological or neurodegenerative condition; a motor neuron disease which requires activation of TrkC; a stroke; a spinal cord injury; an axotomy; or amyotrophic lateral scle-

What is claimed is:

1. A monoclonal antibody that is produced from the hybridoma deposited with the International Depositary Authority of Canada on May 26, 2010 and having accession no. 090310-02, or from a progenitor cell thereof; or, a fragment, portion, variant or derivative thereof, said fragment, portion, variant and derivative thereof comprising all of the 6 CDRs from the monoclonal antibody produced by the hybridoma having accession no. 090310-02.

2. The monoclonal antibody of claim 1, wherein said antibody does not bind the D5 domain of TrkC.

3. The monoclonal antibody or the fragment, portion, variant or derivative of claim 1, wherein the antibody or fragment, portion, variant or derivative activates TrkC.

4. The monoclonal antibody or the fragment, portion, variant or derivative of claim 1, wherein the antibody or the fragment, portion, variant or derivative thereof binds and/or activates human TrkC.

rosis (ALS); or the subject has been injured by a wound, surgery, ischemia, infection, a metabolic disease, malnutrition, a malignant tumor or a toxic drug.

12. The method of claim 11, wherein the subject has a motor neuron disease selected from the group consisting of ALS, progressive bulbar palsy, pseudobulbar palsy, primary lateral sclerosis, progressive muscular atrophy, spinal muscular atrophy, SMA Type I, SMA type II, SMA type III, Fazio-Londe disease, Kennedy disease, congenital SMA with arthrogryposis, and post-polio syndrome.

13. The method of claim 7, wherein the monoclonal antibody or the fragment, portion, variant or derivative is administered to the subject parenterally, intravenously, subcutaneously or interperitoneally.

14. A method for treating ALS in a subject, comprising administering a therapeutically effective amount of the monoclonal antibody or the fragment, portion, variant or derivative of claim 1 to the subject.

15. A method for treating or preventing a neurodegenerative condition or for treating a motor neuron disease in a subject, comprising administering a therapeutically effective amount of the monoclonal antibody or the fragment, portion, variant or derivative of claim 1 to the subject.

16. The monoclonal antibody or fragment, portion, variant or derivative of claim 1, comprising a single-chain antibody and/or a Fab fragment.

17. An antigen-binding fragment of the monoclonal antibody of claim 1 which specifically binds and/or activates TrkC receptor, said antigen-binding fragment comprising all of the 6 CDRs from the monoclonal antibody produced by the hybridoma haying accession no. 090310-02.

18. The monoclonal antibody or the fragment, portion, variant or derivative of claim 1, wherein the antibody, fragment, portion, variant or derivative is humanized, veneered or chimeric.

19. A method of in vitro screening for an agent which binds to TrkC receptor and can thereby affect TrkC receptor biological activity, which comprises:

combining the antibody or the fragment, portion, variant or derivative of claim 1 with TrkC receptor, in the presence or absence of a candidate agent; and determining whether binding of said antibody to TrkC receptor is reduced in the presence of the candidate agent;

wherein a reduction in antibody binding indicates that said candidate agent binds to TrkC receptor, and can thereby affect TrkC receptor biological activity.

20. A hybridoma deposited with the International Depositary Authority of Canada on May 26, 2010 and having accession no. 090310-02 or a progenitor cell thereof.

\* \* \* \* \*